United States Patent
Frederix et al.

(10) Patent No.: US 7,770,437 B2
(45) Date of Patent: Aug. 10, 2010

(54) THIOL OR DISULFIDE MOLECULES HAVING POLY(ETHYLENE OXIDE) GROUPS FOR USE IN A SELF ASSEMBLED MONOLAYER BOUND TO A METAL LAYER FOR COVALENTLY IMMOBILIZING BIOMOLECULES IN A BIOSENSOR

(75) Inventors: Filip Frederix, Leuven (BE); Kristien Bonroy, Averbode (BE); Karolien Jans, Hasselt (BE)

(73) Assignee: IMEC, Leuven (BE)

( * ) Notice: Subject to any disclaimer, the term of this patent is extended or adjusted under 35 U.S.C. 154(b) by 572 days.

(21) Appl. No.: 11/637,390

(22) Filed: Dec. 12, 2006

(65) Prior Publication Data

US 2007/0272003 A1    Nov. 29, 2007

Related U.S. Application Data

(60) Provisional application No. 60/751,383, filed on Dec. 16, 2005.

(51) Int. Cl.
*G01N 37/00* (2006.01)
(52) U.S. Cl. ............ 73/61.41; 134/18; 428/98; 549/554; 562/432; 562/602; 564/248; 568/18
(58) Field of Classification Search ........... 73/61.41; 134/18; 428/98; 549/554
See application file for complete search history.

(56) References Cited

OTHER PUBLICATIONS

Miller et al. (J. Med. Chem. 2004, 47, 4802-4805).*
Samanta et al. (Chem. Commun., 2003, 1186-1187).*
Lahiri et al. (Langmuir 1999, 15, 2055-2060).*

* cited by examiner

*Primary Examiner*—Kamal A Saeed
*Assistant Examiner*—Valerie Rodriguez-Garcia
(74) *Attorney, Agent, or Firm*—Knobbe Martens Olson & Bear LLP

(57) ABSTRACT

An article is provided for immobilizing functional organic biomolecules (e.g. proteins, DNA, and the like) through a covalent bond to a thiolate or disulfide monolayer to a metal surface wherein an extra activation step of the surface layer or an activation step of the functional biomolecules or bioreceptors could be avoided. The article comprises mixed self-assembled monolayers of thiol or disulfide molecules of formula $X_1—(CH_2)_c—O—([CH_2]_t—CH_2—O)_n—R_1—S—X_2$ incorporating poly(ethylene oxide) groups and two functional groups, $X_1$ and $X_2$. Preferably, one functional group resists nonspecific adsorption and the other functional group directly (without activation) reacts with functional groups on the biomolecules. The functional group $X_1$ is selected from the group consisting of flurophenyl, fluorobenzoyl, fluorophenoxycarbonyl, nitrophenoxycarbonyl, $C_{2-12}$ alkenyl, sulfonyl halide, isothiocyanato, isocyanato, carbonyl halide, haloalkylcarbonyl, and diazonium carbonyl. The poly(ethylene oxide) groups resist nonspecific adsorption and enhance the specific affinity interactions. A particularly preferred molecule is 2-(2-{2-[2-(2-{2-[2-(11-mercaptoyldisulfanyl-undecyloxy)ethoxy]ethoxy}ethoxy)ethoxy]ethoxy} acetic acid pentafluorophenyl ester. A sensor device including these monolayers is also provided to perform reproducible, sensitive, specific and stable bioanalysis.

21 Claims, 2 Drawing Sheets

THIOL OR DISULFIDE MOLECULES HAVING POLY(ETHYLENE OXIDE) GROUPS FOR USE IN A SELF ASSEMBLED MONOLAYER BOUND TO A METAL LAYER FOR COVALENTLY IMMOBILIZING BIOMOLECULES IN A BIOSENSOR

CROSS-REFERENCE TO RELATED APPLICATIONS

This application claims the benefit under 35 U.S.C. §119(e) of U.S. provisional application Ser. No. U.S. 60/751,383, filed Dec. 16, 2005, the disclosure of which is hereby expressly incorporated by reference in its entirety and is hereby expressly made a portion of this application.

FIELD OF THE INVENTION

The preferred embodiments relate to the field of sensors, particularly biosensors for detecting an analyte in a sample, especially sensors comprising a metal layer substrate and one or more organic molecules bound to the substrate. The preferred embodiments relate as well to the manufacture of such sensors, and organic molecules suitable for use in such sensors.

BACKGROUND OF THE INVENTION

In the past two decades, the biological and medical fields have discovered the great advantages in the use of biosensors and biochips capable of characterizing and quantifying (bio) molecules. The fastest growing area in biosensors research involves affinity-based biosensors or immunosensors. These sensors are expected to revolutionize in areas like diagnostics, food processing, antiterrorism, environmental monitoring and public health where rapid detection combined to high sensitivity are important.

The development of strategies to immobilize groups of biomolecules to substrates has given rise to the field of biochips and has dramatically increased the rate and scope of discoveries in basic and applied science. A key challenge in biochip technology has been the development of reliable and reproducible chemistries for the immobilization of ligands or bioreceptors to a single substrate.

In order to be broadly useful for the preparation of a wide variety of biochips, the immobilization reaction should have several characteristics. First, the reaction should occur rapidly and therefore allow the use of low concentrations of reagents for immobilization. Second, the chemistry should require little, if any, post-synthetic modifications of ligands before immobilization to maximize the number of compounds that can be generated by solution or by solid-phase synthesis and minimize the cost of these reagents. Third, the immobilization process should occur selectively in the presence of common functional groups, including amines, thiols, carboxylic acids, and alcohols, to ensure that ligands are immobilized in a preferable oriented and homogeneous manner. Finally, the reaction should have well-behaved kinetics and be easily monitored with conventional spectroscopic methods to control the density of ligands on the chip.

Several chemical systems have been described and used for the immobilization of proteins to solid biochip surfaces. The protein coupling chemistry depends upon the underlying substrate of the biochip combined with the desired bioreceptor species one would like to couple to the biochip substrate. A number of methods have therefore been applied for the immobilization of receptor biomolecules, e.g. adsorption, covalent attachment to silanes or mixed layers of thiols, embedding in polymers and membranes. These different kinds of chemistries should be a compromise between the functional groups available on these chemistries and the functional groups available on the bioreceptor species, which one wants to immobilize on the biochip substrate. The groups on the bioreceptor species are important to achieve a random or orientated immobilization of the immobilized bioreceptors It is known in the art of biosensors that molecules having the formula X—R—Ch-M adhered to a surface as part of a self assembled monolayer, where X is a functionality that adheres to the surface, R is a spacer moiety, M is a metal and Ch is a chelating agent for the metal ion M. These monolayers only have a limited surface accessibility for biological binding and oriented immobilization. Moreover, this type of monolayer can only be achieved via an extra cross-linking step.

A method for immobilizing proteins on mixed self-assembled monolayers of alkanethiols is also known in the art. This method needs an activation step comprising forming an N-hydroxysuccinimidyl (NHS) ester from the carboxylic acid groups of the self-assembled monolayer and then coupling this ester to a free amino group of the protein. In a first step, a self-assembling monolayer having free carboxylic acid groups is formed onto a gold surface. In a next step, the surface carboxylic acid groups are activated to form the NHS ester, followed by displacement of the NHS ester with an amino group of the protein to form an amido function. Since several steps have to be performed after deposition of the self-assembling monolayer onto the substrate, the yield reduces after each step, resulting in a low final yield of the immobilization degree.

Self-assembled monolayers with a $CH=CH_2$ end group are also known in the art but no biomolecules or bioreceptors have been coupled to this functional group on a gold surface. In addition, such monolayers do not incorporate poly(ethylene oxide) groups which are desirable to avoid non-specific adsorption, a key issue in biosensing experiments.

Thiolate or disulfide self-assembled monolayers with aldehyde or epoxy end groups, which can be directly coupled to functional groups on biomolecules or bioreceptors are also known in the art. However these self-assembled monolayers do not incorporate poly(ethylene oxide) groups allowing a better sensitivity and specificity of the final biosensor interface.

Self-assembled monolayers with pre-activated groups, e.g. dithio-bis(succinimidylundecanoate), dithio-bis(succinimidylpropionate) and dithio-bis(succinimidylhexadecanoate) are already known in the art and can incorporate poly(ethylene oxide) groups. However the N-hydroxysuccinimidyl group is very sensitive to hydrolysis, which makes it difficult to store these activated samples before use.

Self-assembled monolayers incorporating poly(ethylene oxide) groups and a preactivated maleimidyl group are also known in the art. However a maleimide reacts preferentially with free thinly groups, which are not always readily available in proteins such as antibodies. In order to avoid this drawback, antibodies can be reduced to generate free thinly groups but this additional step is difficult to perform when forming biochips and often decreases the antibody affinity.

Health and environment related fields, faces various biochemical processes, which have to be evaluated rapidly at decreasing detection levels. Many biochemical analytical methods involve immobilization of a biological molecule on a surface. The increasing miniaturization and the demand for sensitivity require a covalent immobilization of biomolecules. Affinity biosensor transducers are defined as systems containing at least one biological element able to recognize an analyte. This element is called the biological recognition layer and consists of a probe molecule, covalently bound to a linking layer, which makes the connection with the transducer. The substrate can be a deposit of a metal film on any convenient support or any other solid surface able to selectively bind monolayers. Preferred metals include gold, silver, Ga—As alloys, palladium, platinum, copper, and the like. Silanes and alkyl phosphate monolayers can also be used on oxide material substrates like $SiO_2$, $Nb_2O_5$, $TiO_2$, $ZrO_2$, $Al_2O_3$, and $Ta_2O_5$. A biosensor must respond to major qualities like stability, specificity, selectivity, and reproducibility. For all those reasons, only few affinity biosensors are commercially available. The major challenge is the realization of new specific and selective self-assembled monolayers and the receptors. An analyte must be detectable in an excess of other proteins. The most common receptors are antibodies and specific binding proteins which have a reversible specific binding affinity for an analyte. Chemical modifications of the surface moieties may create. new surface functionalities, such as, for example, amine-terminated functional groups appropriate for particular diagnostic or therapeutic operations.

SUMMARY OF THE INVENTION

New organic molecules are provided suitable for forming a self-assembling monolayer onto a surface, in particular a metal surface, while solving one or more of the problems identified herein above. A method is also provided for forming mixed self-assembled monolayers of thiols or disulfide molecules incorporating poly(ethylene oxide) groups and two functional groups, preferably wherein one functional group is pre-activated and can be directly and covalently coupled to the amino groups of a bioreceptor while the other functional group provides resistance to non-specific adsorption. Organic molecules are provided that can form self-assembling monolayers suitable for making high selectivity, high stability and/or high reproducibility sensor substrates linked to a recognition molecule. In addition these organic molecules should decrease non-specific binding and allow binding of a receptor molecule onto the self-assembling monolayer in one single step.

In a first aspect, an organic molecule is provided having the structural formula $X_1$—$(CH_2)_c$—O—$([CH_2]_t$—$CH_2$—O$)_n$—$R_1$—S—$X_2$, wherein:

$X_2$ is either H or S—$R_5$, $R_5$ is an organic spacer selected from the group consisting of $R_2$—(O—$CH_2$—$[CH_2]_t)_n$—O—$(CH_2)_c$—$X_1'$ and $R_3$—(O—$CH_2$—$[CH_2]_t)_n$—$Y_1$, t is 1 or 2, c is an integer from 0 to 3, n is an integer from 3 to 15,000, $R_1$, $R_2$ and $R_3$ are each independently a saturated or ethylenically unsaturated hydrocarbyl group with 3 to 30 carbon atoms selected from the group consisting of alkyl, alkenyl, cycloalkyl, cycloalkyl-alkyl, cycloalkenyl, cycloalkenylalkyl and cycloalkylalkenyl, said group optionally comprising one or more heteroatoms selected from nitrogen, oxygen and sulfur in the main chain, and said group optionally comprising one or more oxo substituents, $Y_1$ is either hydroxy or methoxy, $X_1$ and $X_1'$ are each independently selected from the group consisting of fluorophenyl, fluorobenzoyl, fluorophenoxycarbonyl, nitrophenoxycarbonyl, oxiranyl, aziridinyl, $C_{2-12}$ alkenyl, imino-ether, dichlorotriazinyl, sulfonyl halide, alkoxycarbonyl, isothiocyanato, isocyanato, carbonyl halide, haloalkylcarbonyl, carboxylic acid anhydride, diazonium carbonyl, N-(2-oxotetrahydro-3-thienyl)amido and N-carboxy-thiazolidinyl-2-thione.

In one embodiment of the first aspect, $X_1$ represents a group which can directly react with a biomolecule, i.e. without prior activation of either the organic molecule of preferred embodiments or the biomolecule to be immobilized. In a preferred embodiment, the biomolecule has at least one primary amino-group, which can react with the $X_1$ group. In another preferred embodiment, the amino group of a lysine amino acid of a protein/peptide or the amino group at the end of a DNA or RNA strand or oligo nucleic acid chain can react with the molecule $X_1$—$(CH_2)_c$—O—$([CH_2]_t$—$CH_2$—O$)_n$—$R_1$—S—$X_2$ at the $X_1$ side of the molecule.

The group —$([CH_2]_t$—$CH_2$—O$)_n$— in $X_1$—$(CH_2)_c$—O—$([CH_2]_t$—$CH_2$—O$)_n$—$R_1$—S—$X_2$ and in $R_2$—(O—$CH_2$—$[CH_2]_t)_n$—O—$(CH_2)_c$—$X_1'$ is preferably selected in such a way that non-specific adsorption of a biomolecules to the organic molecule of preferred embodiments is substantially avoided.

$X_1$ and $X_1'$ each independently include a chemical group compatible with monolayer formation and which needs no in situ activation prior to reaction with the biological moiety.

In a second aspect, a device for immobilizing at least one biomolecule through a covalent bond is provided, said device comprising:

a substrate comprising a metal layer, one or more first species bound onto said metal layer, wherein each of said one or more first species is a molecule having a structural formula $X_1$—$(CH_2)_c$—O—$([CH_2]_t$—$CH_2$—O$)_n$—$R_1$—S-M, wherein M is said metal layer to which said one or more molecules are bounded, t is an integer from 1 to 2, n is an integer from 3 to 15,000, c is an integer from 0 to 3

$R_1$ is a saturated or ethylenically unsaturated hydrocarbyl group with 3 to 30 carbon atoms selected from the group consisting of alkyl, alkenyl, cycloalkyl, cycloalkylalkyl, cycloalkenyl, cycloalkenylalkyl and cycloalkylalkenyl, said group optionally comprising one or more heteroatoms selected from nitrogen, oxygen and sulfur in the main chain, and said group optionally comprising one or more oxo substituents, $X_1$ is selected from the group consisting of fluorophenyl, fluorobenzoyl, fluorophenoxycarbonyl, nitrophenoxycarbonyl, oxiranyl, aziridinyl, $C_{2-12}$ alkenyl, imino-ether, dichlorotriazinyl, sulfonyl halide, alkoxycarbonyl, isothiocyanato, isocyanato, carbonyl halide, haloalkylcarbonyl, carboxylic acid anhydride, diazonium carbonyl, N-(2-oxotetrahydro-3-thienyl)amido and N-carboxy-thiazolidinyl-2-thione.

In an embodiment of the second aspect, the device further comprises a second species, the second species being bound onto the metal layer and including a compound having the chemical formula:

$Y_1$—$([CH_2]_t$—$CH_2$—O$)_n$—$R_3$—S-M wherein:

$R_3$ is a saturated or ethylenically unsaturated hydrocarbyl group with 3 to 30 carbon atoms selected from the group consisting of alkyl, alkenyl, cycloalkyl, cycloalkylalkyl, cycloalkenyl, cycloalkenylalkyl and cycloalkylalkenyl, said group optionally comprising one or more heteroatoms selected from nitrogen, oxygen and sulfur in the main chain, and said group optionally comprising one or more oxo substituents, t is an integer from 1 to 2, n is an integer from 3 to 15,000, M is the metal of said metal layer, and $Y_1$ is either a hydroxy group or a methoxy group.

The second species is preferably selected such that non-specific adsorption of biomolecules is substantially avoided.

In a third aspect, a process for preparing a device according to the second aspect is provided. This process comprises the steps of:

a) providing a metal layer, b) contacting said metal layer with one or more molecules according to the first aspect, wherein said one or more molecules self-assemble to form a layer of one or more first species bound onto said metal layer, wherein each of said one or more first species is a molecule having a structural formula $X_1$—$(CH_2)_c$—O—$([CH_2]_t$—$CH_2$—$O)_n$—$R_1$—S-M, wherein M is said metal layer to which said one or more molecules are bounded, t is an integer from 1 to 2, n is an integer from 3 to 15,000, c is an integer from 0 to 3, $R_1$ is a saturated or ethylenically unsaturated hydrocarbyl group with 3 to 30 carbon atoms selected from the group consisting of alkyl, alkenyl, cycloalkyl, cycloalkyl-alkyl, cycloalkenyl, cycloalkenylalkyl and cycloalkylalkenyl, said group optionally comprising one or more heteroatoms selected from nitrogen, oxygen and sulfur in the main chain, and said group optionally comprising one or more oxo substituents, $X_1$ is selected from the group consisting of fluorophenyl, fluorobenzoyl, fluorophenoxycarbonyl, nitrophenoxycarbonyl, oxiranyl, aziridinyl, $C_{2-12}$ alkenyl, imino-ether, dichlorotriazinyl, sulfonyl halide, alkoxycarbonyl, isothiocyanato, isocyanato, carbonyl halide, haloalkylcarbonyl, carboxylic acid anhydride, diazonium carbonyl, N-(2-oxotetrahydro-3-thienyl) amido and N-carboxy-thiazolidinyl-2-thione.

In a fourth aspect, a process for preparing a device according to an embodiment of the second aspect is provided, comprising the steps of:

a) providing a metal layer, b) contacting said metal layer with one or more molecules according to the first aspect and with one or more molecules having a formula $Y_1$-$([CH_2]_t$—$CH_2$—$O)_n$—$R_3$—S—$Y_2$, wherein said one or more molecules according to the first aspect and said one or more molecules having a formula $Y_1$-$([CH_2]_t$—$CH_2$—$O)_n$—$R_3$—S—$Y_2$ self-assemble to form a mixed layer of one or more first species and one or more second species bound onto said metal layer, wherein each of said one or more first species is a molecule having a structural formula $X_1$—$(CH_2)_c$—O—$([CH_2]_t$—$CH_2$—$O)_n$—$R_1$—S-M and each of said one or more second species is a molecule $Y_1$-$([CH_2]_t$—$CH_2$—$O)_n$—$R_3$—S-M wherein:

$Y_2$ is either H or —S—$R_4$—(O—$CH_2$—$[CH_2]_t)_n$—$Y_1$', $R_1$, $R_3$ and $R_4$ are each independently a saturated or ethylenically unsaturated hydrocarbyl group with 3 to 30 carbon atoms selected from the group consisting of alkyl, alkenyl, cycloalkyl, cycloalkylalkyl, cycloalkenyl, cycloalkenylalkyl and cycloalkylalkenyl, said group optionally comprising one or more heteroatoms selected from nitrogen, oxygen and sulfur in the main chain, and said group optionally comprising one or more oxo substituents, $Y_1$ and $Y_1$' are independently either a hydroxy group or a methoxy group, M is said metal layer to which said one or more molecules are bounded, t is an integer from 1 to 2, n is an integer from 3 to 15,000, c is an integer from 0 to 3, and $X_1$ is selected from the group consisting of fluorophenyl, fluorobenzoyl, fluorophenoxycarbonyl, nitrophenoxycarbonyl, oxiranyl, aziridinyl, $C_{2-12}$ alkenyl, imino-ether, dichlorotriazinyl, sulfonyl halide, alkoxycarbonyl, isothiocyanato, isocyanato, carbonyl halide, haloalkylcarbonyl, carboxylic acid anhydride, diazonium carbonyl, N-(2-oxotetrahydro-3-thienyl) amido and N-carboxy-thiazolidinyl-2-thione.

In a fifth aspect, a sensor is provided for the detection of an analyte in a sample fluid, the sensor comprising:

a device according to the second aspect on which at least one biomolecule is immobilized by a covalent bound, and a transducer.

In a sixth aspect, a method for manufacturing a sensor according to the fifth aspect is provided, wherein the method comprises the steps of:

contacting a device according to the second aspect with a solution of at least one biomolecule, connecting said device to a transducer.

In an embodiment of this sixth aspect, the at least one biomolecule has at least one primary amino group. In another embodiment of this sixth aspect, the device and/or said at least one biomolecule is not chemically activated prior to contacting.

DETAILED DESCRIPTION OF THE PREFERRED EMBODIMENT

Definitions

Figure 1:
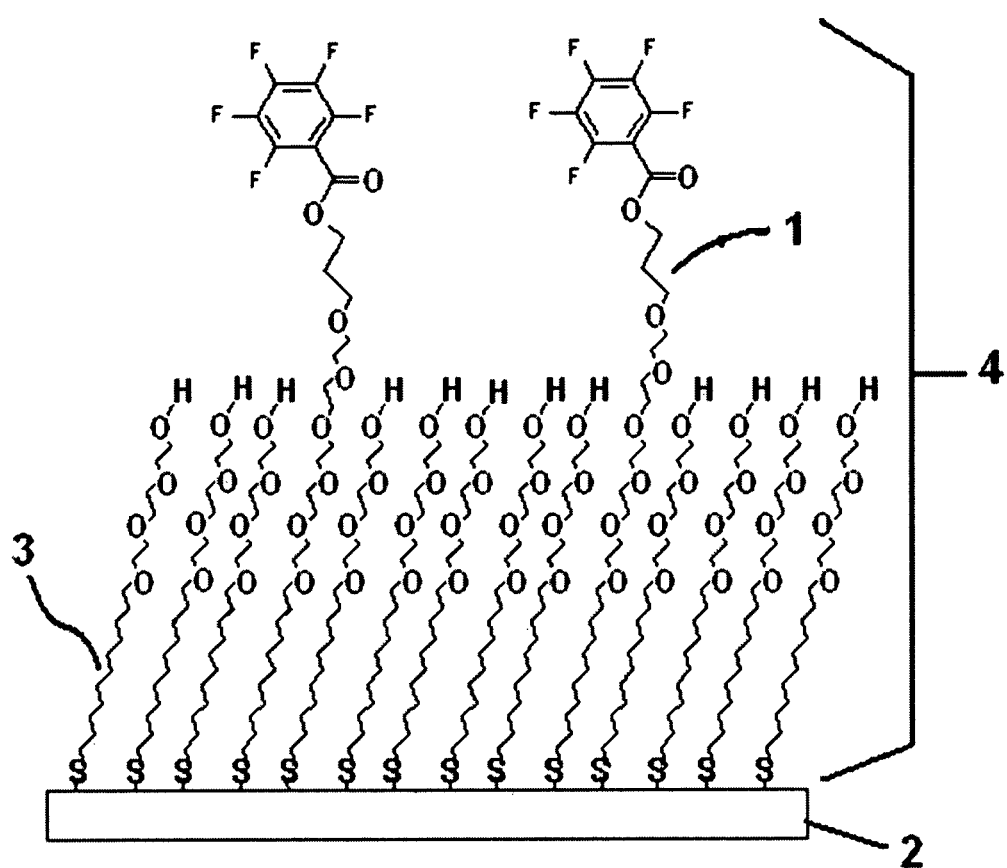
FIG. 1 represents schematically a device according to an embodiment of the second aspect.

As used herein and unless stated otherwise, the term "self-assembling" relates the association of molecules without guidance or management from an outside source. It results in a layer, usually a monolayer of those molecules on a surface.

As used herein and unless stated otherwise, the terms "metal layer" relates to a layer made from one or more metals or metal alloys, having a thickness of from 1 nm to 10 nm (but not limited hereto) and which can be either self supported or supported by a substrate. If the layer is self-supported, it can be named "substrate" as well.

As used herein and unless stated otherwise, the term "hydrocarbyl group" relates to a saturated or ethylenically unsaturated, cyclic or non-cyclic chain selected from the group consisting of alkyl, alkenyl, cycloalkyl, cycloalkenyl cycloalkyl-alkyl, cycloalkenyl-alkyl and cycloalkyl-alkenyl; when non-cyclic, this chain can be linear or branched.

The following description and examples illustrate a preferred embodiment of the present invention in detail. Those skilled in the art will recognize that there are numerous variations and modifications of this invention that are encompassed by its scope. Accordingly, the description of a preferred embodiment should not be deemed to limit the scope of the present invention.

In a first aspect, an organic molecule is provided with the structural formula:

$$X_1\text{—PEO1-}R_1\text{—S—}X_2$$

wherein:
  $X_2$ is hydrogen, —S—$R_2$—PEO2-$X_1$ or —S—$R_2$—PEO2-$X_1'$, and
  $X_1$ and $X_1'$ are as defined herein-above, and
  $R_1$ and $R_2$ are selected such that a stable ordered monolayer is formed.

$R_1$ and $R_2$ independently include a spacer. $R_1$ and $R_2$ can be the same or different. $R_1$ and $R_2$ can have the same chemical composition such that a symmetrical molecule is formed. Symmetrical molecules have generally the advantage of a more straightforward synthesis. R1 and R2 preferably promote the formation of a self-assembling monolayer and can be a hydrocarbon chain, i.e. a hydrocarbyl group. The hydrocarbyl group can include n carbon atoms, n being an integer higher (or equal to) 3, 6, 8, or 10, preferably from 3 to 30. The spacer can also represent a hydrocarbyl group interrupted by a —CO— (ketone), —CONH, —CONHCO—, —CSNH—, —CS—, and the like. For instance the hydrocarbyl group can optionally comprise one or more carboxy groups in the main chain of the hydrocarbyl group. The hydrocarbyl group can also be interrupted by one or more heteroatoms. The heteroatom can be selected from the group consisting of —N—, —O—, and —S—. In particular, the heteroatom can be O. For instance, $R_1$ and $R_2$ can independently comprise one or more heteroatoms in the main chain of the hydrocarbyl group. The hydrocarbyl group can also be branched. The spacer can include a first part which is a hydrocarbon chain and a second part which is a hydrocarbyl group interrupted by a heteroatom such as oxygen.

In an advantageous embodiment, $R_1$ and $R_2$ independently include an alkyl chain —$(CH_2)_n$—, n being an integer from 3 to 30, for instance from 3 to 25, preferably from 3 to 20, e.g. from 5 to 20, or from 8 to 16. In another advantageous embodiment, n is an integer. In a preferred embodiment n is higher than 4, higher than 6, higher than 8, higher than 10, higher than 11, higher than 12, higher than 13, higher than 15 or higher than 20. Alternatively, n is an integer from 8 to 16, from 10 to 16.

In a preferred embodiment $R_1$ and $R_2$ are each independently a saturated or ethylenically unsaturated hydrocarbyl group with 3 to 30 carbon atoms selected from the group consisting of alkyl, alkenyl, cycloalkyl, cycloalkyl-alkyl, cycloalkenyl, cycloalkenylalkyl and cycloalkylalkenyl, said group optionally comprising one or more heteroatoms selected from nitrogen, oxygen and sulfur in the main chain, and said group optionally comprising one or more oxo substituents.

PEO1 and PEO2 independently include a —(O—$CH_2$—$[CH_2]_1)_n$—O— group, n being an integer from 3 to 15,000, preferably from 3 to 1250. PEO1 and PEO2 are preferably selected such that non-specific adsorption of chemical molecules is avoided. PEO1 and PEO2 independently include (O—$CH_2$-$[CH_2]_t)_n$—O— such as e.g. (O—$CH_2$—$CH_2$—$)_n$—O—, n being an integer from 3 to 15,000, preferably from 3 to 1250, from 3 to 1000, from 3 to 500, from 3 to 100, from 3 to 50, from 3 to 30, from 3 to 20, from 3 to 15, from 3 to 10, from 3 to 8, or from 2 to 8. Alternatively, n is an integer from 1 to 30, from 1 to 20, from 1 to 15, from 1 to 10, from 1 to 8, or from 1 to 6. t is an integer of from 1 to 10, preferably 1 or 2.

In a particular embodiment, PEO1 is represented by the structural formula —$(CH_2)_c$—O—$([CH_2]_t$—$CH_2$—O$)_n$ and PEO2 is independently from PEO1 represented by the structural formula —(O—$CH_2$—$[CH_2]_t)_n$—O—$(CH_2)_c$—, n being an integer and c being an integer. The groups of formula —(O—$CH_2$—$[CH_2]_t)_n$ are intended for avoiding non-specific adsorption. The variable "n" is preferably from 1 to 10, or more preferably from 1 to 8. The variable "c" is an integer of from 0 to 3, preferably from 1 to 3. Preferably c can be 1, 2, or 3. The variable "t" is 1 or 2.

$X_1$ is a chemical group suitable for binding biological moieties (e.g. a biomolecule) onto a monolayer. More specifically, $X_1$ is a highly reactive functional moiety compatible with monolayer formation and which needs no in situ activation prior to reaction with the biological moiety. The biological moieties that are covalently bound or adsorbed onto the monolayer can be, but are not limited to, nucleic acid strands (DNA, PNA, RNA), proteins, hormones, antibiotics, antibodies, chemically or enzymatically modified antibodies, VHH fragments of lama antibodies, synthetic receptors, single chain Fv's, antigens, enzymes, drugs, drugs of abuse. In general, these biological moieties will serve as a biological sensing element and will be part of a sensor. The resulting sensor will be suitable for determining the presence of a compound, such as a target molecule, which interacts with the biological sensing element. The target molecule could be, but is not limited to, complementary nucleic acid strands (DNA, PNA, RNA), proteins, hormones, antibiotics, antibodies, antigens, enzymes, drugs, drugs of abuse or molecules such as specific molecules present in for example gases and liquids.

$X_1$ includes preferably a chemical group selected from the group consisting of fluorophenyl, fluorobenzoyl, fluorophenoxycarbonyl, nitrophenoxycarbonyl, oxirane, aziridine, $C_{2-12}$ alkenyl, imino-ether, dichlorotriazinyl, sulfonyl halide, alkoxycarbonyl, isothiocyanato, isocyanato, carbonyl halide, haloalkylcarbonyl, carboxylic acid anhydride, diazonium carbonyl, N-(2-oxotetrahydro-3-thienyl)amido and N-carboxy-thiazolidine-2-thione.

For instance, $X_1$ may include one of the following species:

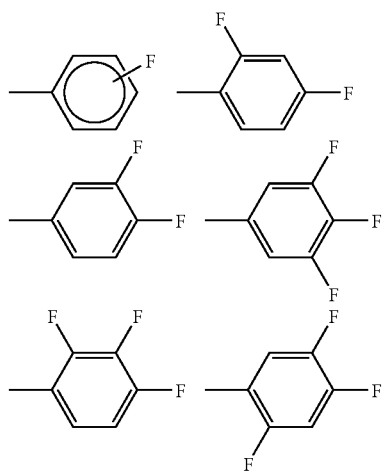

-continued
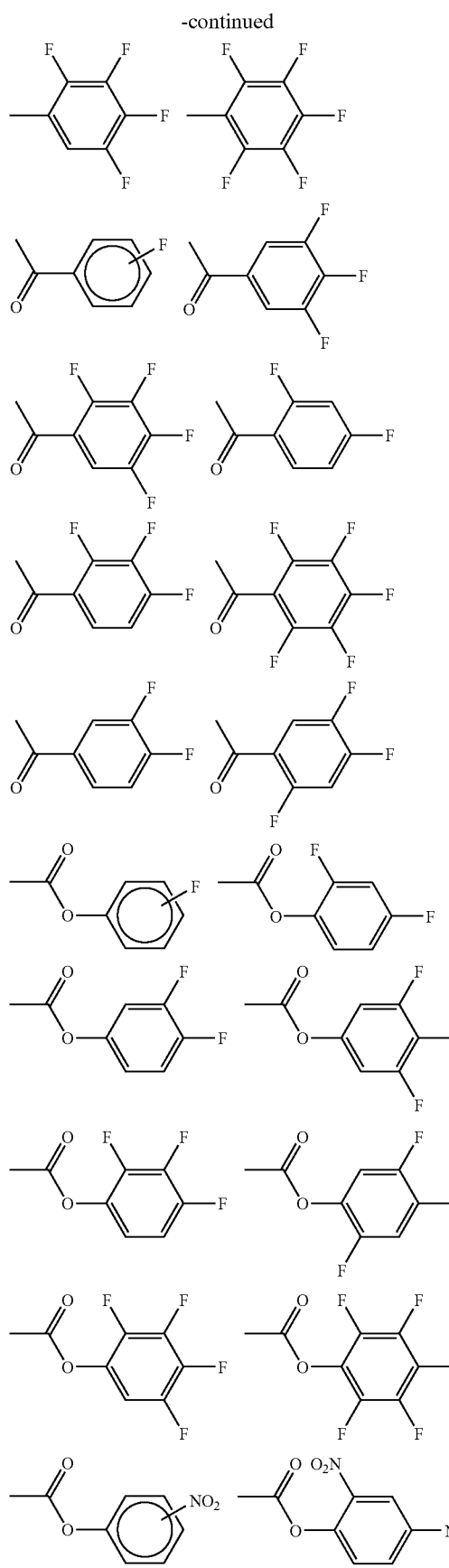
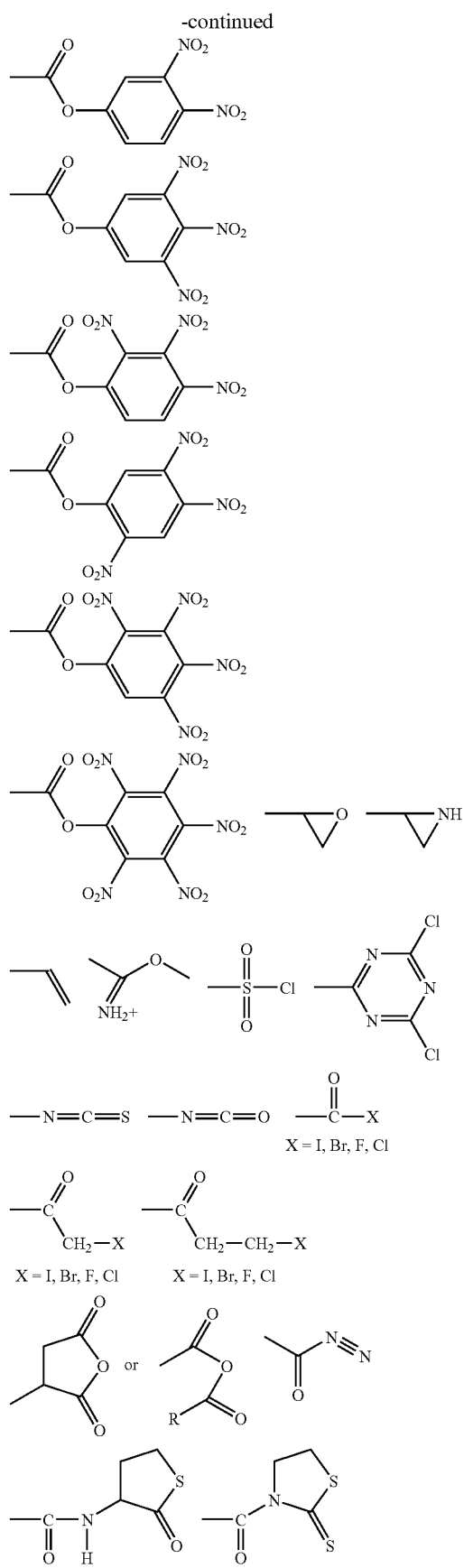

-continued

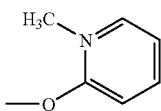

wherein R is either $CH_3$, $CH_2$ or $OCH_2CH_3$.

$X_1$ is a chemical group for binding biological moieties to the molecule as described in the first aspect. The chemical group $X_1$ is used for immobilization of a molecule, e.g. a recognition molecule. The recognition molecule can be e.g. a biomolecule. The recognition molecules can chemically interact (e.g. bind) to the group $X_1$ and in particular the $NH_2$ group of a recognition molecule can bind to the group $X_1$ or can react with the group $X_1$ to bind to molecule $X_1$—$(CH_2)_c$—O—$([CH_2]_t$—$CH_2$—O$)_n$—$R_1$—S—$X_2$.

More specifically, $X_1$ is a highly reactive functional moiety compatible with monolayer formation and which needs no in situ activation prior to reaction with the biological moiety. The biological moieties that can covalently be bound or adsorbed to the chemical molecule as in the first aspect can be, but are not limited to, nucleic acid strands (DNA, PNA, RNA), proteins, hormones, antibiotics, antibodies, chemically or enzymatically modified antibodies, VHH fragments of lama antibodies, synthetic receptors, single chain Fv's, antigens, enzymes, drugs, drugs of abuse. In general, these biological moieties will serve as a biological recognition molecule.

It should be understood that the scope of the molecule as described in the first aspect comprises all possible combinations of chemical groups and elements as specified herein.

In one particular embodiment, the molecule having the structural formula X1-PEO1-R1-S—X2 corresponds to the structural formula X1-$(CH2)_c$-PEO1-R1-S—X2. In another embodiment, the structural formula X1-PEO1-R1-S—X2 corresponds to the structural formula X1-$(CH2)_c$-O—([CH2]t-CH2-O)n-R1-S—X2 wherein $X_2$ is either H or S—$R_5$, $R_5$ is an organic spacer selected from the group consisting of $R_2$—(O—$CH_2$—$[CH_2]_t)_n$—O—$(CH_2)_c$—$X_1$' and $R_3$—(O—$CH_2$—$[CH_2]_t)_n$—$Y_1$, t is 1 or 2, c is an integer from 0 to 3, n is an integer from 3 to 15,000, $R_1$, $R_2$ and $R_3$ are each independently a saturated or ethylenically unsaturated hydrocarbyl group with 3 to 30 carbon atoms selected from the group consisting of alkyl, alkenyl, cycloalkyl, cycloalkyl-alkyl, cycloalkenyl, cycloalkenylalkyl and cycloalkylalkenyl, said group optionally comprising one or more heteroatoms selected from nitrogen, oxygen and sulfur in the main chain, and said group optionally comprising one or more oxo substituents, $Y_1$ is either hydroxy or methoxy, $X_1$ and $X_1$' are each independently selected from the group consisting of fluorophenyl, fluorobenzoyl, fluorophenoxycarbonyl, nitrophenoxycarbonyl, oxiranyl, aziridinyl, $C_{2-12}$ alkenyl, imino-ether, dichlorotriazinyl, sulfonyl halide, alkoxycarbonyl, isothiocyanato, isocyanato, carbonyl halide, haloalkylcarbonyl, carboxylic acid anhydride, diazonium carbonyl, N-(2-oxotetrahydro-3-thienyl)amido and N-carboxy-thiazolidinyl-2-thione.

The functional group —S—S— or H—S— is able to adhere (i.e. chemisorb) to a surface such as a metal layer and can chemically interact (e.g. bind) with said metal layer. For instance, a covalent bond S-M, with S being a sulfur atom and M being the metal, can be formed. The interaction between the sulfur atom and the substrate is well known to people skilled in the art.

In a second aspect, a device, suitable for the fabrication of a sensor in disclosed. The device comprises:

a substrate comprising a metal layer, a first species being attached to the metal layer, the first species including a chemical molecule as in the first aspect, wherein the sulfur atoms of the chemical molecule bind to the metal surface.

In an embodiment of this second aspect, a device for immobilizing at least one biomolecule through a covalent bond is provided, the device comprising:

a substrate comprising a metal layer, one or more first species bound onto said metal layer, wherein each of said one or more first species is a molecule having a structural formula $X_1$—$(CH_2)_c$—O—$([CH_2]_t$—$CH_2$—O$)_n$—$R_1$—S-M, wherein M is said metal layer to which said one or more molecules are bounded, t is an integer from 1 to 2, n is an integer from 3 to 15,000, c is an integer from 0 to 3, $R_1$ is a saturated or ethylenically unsaturated hydrocarbyl group with 3 to 30 carbon atoms selected from the group consisting of alkyl, alkenyl, cycloalkyl, cycloalkyl-alkyl, cycloalkenyl, cycloalkenylalkyl and cycloalkylalkenyl, said group optionally comprising one or more heteroatoms selected from nitrogen, oxygen and sulfur in the main chain, and said group optionally comprising one or more oxo substituents, $X_1$ is selected from the group consisting of fluorophenyl, fluorobenzoyl, fluorophenoxycarbonyl, nitrophenoxycarbonyl, oxiranyl, aziridinyl, $C_{2-12}$ alkenyl, iminoether, dichlorotriazinyl, sulfonyl halide, alkoxycarbonyl, isothiocyanato, isocyanato, carbonyl halide, haloalkylcarbonyl, carboxylic acid anhydride, diazonium carbonyl, N-(2-oxotetrahydro-3-thienyl)amido and N-carboxy-thiazolidinyl-2-thione.

In another embodiment of the second aspect, the device as in the second aspect further comprises a second species, said second species being bound to the metal surface (i.e. the metal layer), the second species being obtained by contacting the metal layer with a compound of the structural formula:

$Y_1$—$R_3$—S—$Y_2$ wherein:

$Y_2$ is hydrogen or —S—$R_4$—$Y_1$, said sulfur atoms covalently bind to the metal layer, and wherein $R_3$ and $R_4$ independently include a spacer including m carbon atoms, m being an integer from 3 to 30, The spacer promotes the formation of a self-assembling monolayer and may be a hydrocarbon chain as defined herein above. $R_3$ and $R_4$ can have the same chemical composition such that a symmetrical molecule is formed. In an embodiment, $R_3$ and $R_4$ are each independently a spacer of m carbon atoms, m being an integer from 3 to 30, from 3 to 25, from 3 to 20, from 5 to 20, or from 8 to 16. The total number of carbon atoms m is preferably higher than 3, higher than 6, higher than 8, or higher than 10.

Optionally, $R_3$ and $R_4$ may include q heteroatoms wherein (m+q) is an integer preferably higher than 6. In a preferred embodiment, $R_3$ and $R_4$ are independently selected from the group consisting of alkyl chains $(CH_2)_m$ with m being an integer higher than 6 and alkyl chains including q heteroatoms, q being an integer such that (m+q) is higher than 6.

In another embodiment, $R_3$ and $R_4$ are each independently from each other a spacer including two parts, a first part for obtaining a stable ordered monolayer and a second part for avoiding non-specific adsorption. In a particular embodiment, $R_3$ and $R_4$ are independently from each other $(CH_2)_e$—$(CH_2$—$CH_2$—$O)_f$—$(CH_2)_g$, e being an integer, f being an integer and g being an integer. The alkyl chain is intended to achieve a stable ordered and reproducible system while the polyethylene oxide groups are intended for avoiding non-specific adsorption. The variable "e" is preferably an integer from 1 to 20, from 5 to 20, from 5 to 15, or from 5 to 12, e.g. 6 or 11. The variable "f" is preferably an integer from 1 to 10, from 1 to 8, or from 2 to 6, e.g. 3, 4 or 5. The variable "g" is an integer preferably from 0 to 3, e.g. 1 or 2.

In other words, in this embodiment of the second aspect, the device as in the second aspect further comprising one or more second species bound onto said metal layer, wherein each of said one or more second species is a molecule having a structural formula $Y_1$—$([CH_2]_t$—$CH_2$—$O)_n$—$R_3$—S-M wherein:

$R_3$ is a saturated or ethylenically unsaturated hydrocarbyl group with 3 to 30 carbon atoms selected from the group consisting of alkyl, alkenyl, cycloalkyl, cycloalkylalkyl, cycloalkenyl, cycloalkenylalkyl and cycloalkylalkenyl, said group optionally comprising one or more heteroatoms selected from nitrogen, oxygen and sulfur in the main chain, and said group optionally comprising one or more oxo substituents, t is an integer from 1 to 2, n is an integer from 3 to 15,000, M is the metal of said metal layer, and $Y_1$ is either a hydroxy group or a methoxy group.

The first species and the second species are selected such that a mixed self-assembled layer such as a mixed self-assembled monolayer is formed on the metal layer. A mixed self-assembled monolayer results in better sensitivity of the recognition molecule towards the target molecule in the medium.

The molar ratio of the second species to the first species can be 1000:1, 500:1, 100:1, 80:1, 70:1, 60:1, 50:1, 20:1, 10:1, 5:1, 95:5, 90:10, 80:20, 70:30, or 60:40, and can be determined by spectroscopic techniques available to a person skilled in the art.

Non-specific adsorption is preferably avoided when the device is used as a sensor. Non-specific adsorption herein refers to interaction between the recognition molecule immobilized at the surface and any species being present in a medium that preferably contains the target molecule. Such "any species" excludes the target molecule.

In advantageous embodiments, the first species has the structural formula as in any of the examples. The substrate may comprise a metal layer comprising, but not limited hereto, gold, silver, mercury, aluminum, platinum, palladium, copper, cadmium, lead, iron, chromium, manganese, tungsten and alloys thereof. The substrate can be the metal layer itself. The substrate can also be a sensor, a biosensor, a DNA chip, a protein chip, a microarray, a microscope slide, a silicon wafer or a microelectronic surface. The substrate can be a part of a transducer, which can be, but is not limited to, a Surface Plasmon Resonance sensor, a Surface Acoustic Wave sensor, a Quartz Crystal Microbalance, an amperometric sensor, a capacitive sensor, an Interdigitated Electrode or a ChemFET sensor. The surface can also have magnetic properties such as a magnetic particle comprising a magnetic material such $Fe_2O_3$ or $Fe_3O_4$, optionally coated with a coating layer, preferably a metal coating layer.

The first species forms a self-assembling monolayer onto the surface of the device. Self-assembled monolayers are considered as a relative ordered assembly of molecules that spontaneously attach (or chemisorb) onto a surface. Molecules are preferably oriented parallel or preferably under an angle with respect to the surface.

Each group being part of a self-assembling monolayer preferably includes a functional group for attaching to the surface and a functional group that binds to the recognition molecule. In the preferred embodiments, the functional group being able to attach to the surface is a disulfide group —S—S— or a thinly group, and the functional group being able to bind a recognition molecule (e.g. to react with a recognition molecule in order to bind to the molecule) is the group $X_1$ as defined herein above. The functional group —S—S— or HS— is able to adhere (chemisorb) to a surface such as a metal and can chemically interact with the metal surface. Interaction between the sulfur atom and the substrate is well known to people skilled in the art. The chemical group $X_1$ is used for surface immobilization of a recognition molecule. The recognition molecules can be bound to this group and in particular, a $NH_2$ group (i.e. at least one primary amino group) of a recognition molecule can react with the first species, i.e. with the group X1 present on this first species.

FIG. 1 represents schematically a device according to an embodiment of the second aspect. This device comprises a metal layer (2) on which a first species (1) and a second species (3) are bound. The first and the second species form a monolayer (4) on the metal layer (2).

In a third aspect, a process for preparing a device according to the second aspect is provided. This process comprises the steps of:

a) providing a metal layer, b) contacting said metal layer with one or more molecules according to the first aspect, wherein said one or more molecules self-assemble to form a layer of one or more first species bound onto said metal layer, wherein each of said one or more first species is a molecule having a structural formula $X_1$—$(CH_2)_c$—O—$([CH_2]_t$—$CH_2$—$O)_n$—$R_1$—S-M, wherein M is said metal layer to which said one or more molecules are bounded, t is an integer from 1 to 2, n is an integer from 3 to 15,000, c is an integer from 0 to 3, $R_1$ is a saturated or ethylenically unsaturated hydrocarbyl group with 3 to 30 carbon atoms selected from the group consisting of alkyl, alkenyl, cycloalkyl, cycloalkylalkyl, cycloalkenyl, cycloalkenylalkyl and cycloalkylalkenyl, said group optionally comprising one or more heteroatoms selected from nitrogen, oxygen and sulfur in the main chain, and said group optionally comprising one or more oxo substituents, $X_1$ is selected from the group consisting of fluorophenyl, fluorobenzoyl, fluorophenoxycarbonyl, nitrophenoxycarbonyl, oxiranyl, aziridinyl, $C_{2-12}$ alkenyl, iminoether, dichlorotriazinyl, sulfonyl halide, alkoxycarbonyl, isothiocyanato, isocyanato, carbonyl halide, haloalkylcarbonyl, carboxylic acid anhydride, diazonium carbonyl, N-(2-oxotetrahydro-3-thienyl)amido and N-carboxy-thiazolidinyl-2-thione.

Preferably, a treatment to remove any metal oxide layer present at the surface of the metal layer is performed according to any method well known by the person skilled in the art.

Figure 2:
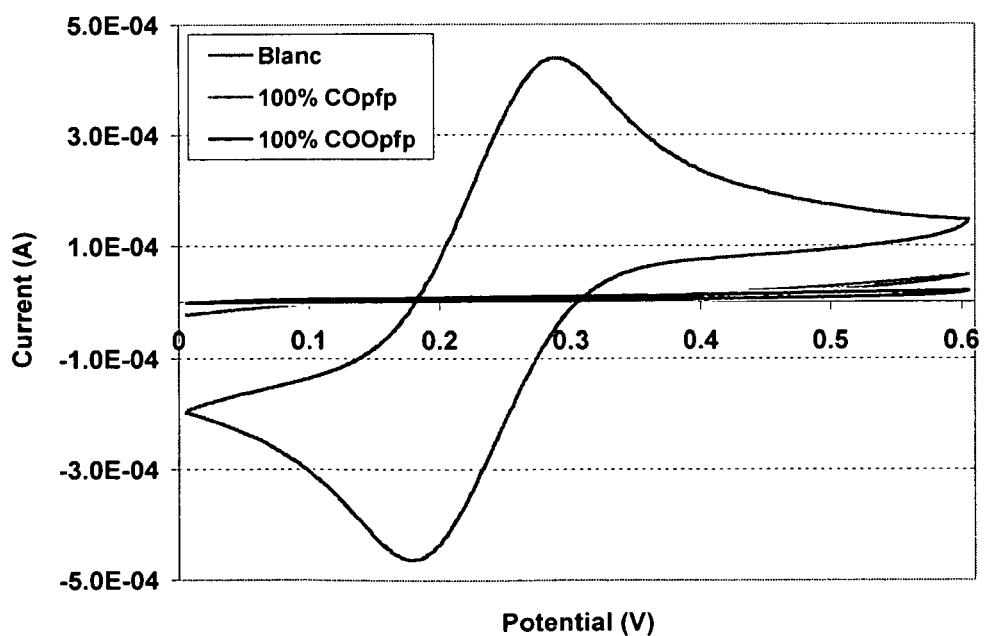
FIG. 2 shows cyclic voltammograms (CV) of a gold layer with and without molecules according to an embodiment.

FIG. 2 shows a cyclic voltammogram (CV) of a gold layer without a mono-layer of molecules on its surface (Blanc, light line), a CV of the same gold layer on which a mono-layer of molecules according to Example 7 has been self-assembled (100% COpfp doted line) and a CV of the same gold layer on which a mono-layer of molecules according to Example 8 has been self-assembled (100% COOpfp, dark line). The signal of the current in CVs of the gold layers on which a mono-layer of molecules according to the preferred embodiments has been formed, show a dramatic decrease when compared with the signal of the current recorded for the gold surface alone. This indicates a substantially complete coverage of the gold layer by the respective self-assembled mono-layers.

In a fourth aspect, a process is provided for preparing a device according to an embodiment of the second aspect, comprising the steps of:
a) providing a metal layer,
b) contacting said metal layer with one or more molecules according to claim 1 and with one or more molecules having a formula $Y_1$-$([CH_2]_t$—$CH_2$—$O)_n$—$R_3$—$S$—$Y_2$,
wherein said one or more molecules according to claim 1 and said one or more molecules having a formula $Y_1$—$([CH_2]_t$—$CH_2$—$O)_n$—$R_3$—$S$—$Y_2$ self-assemble to form a mixed layer of one or more first species and one or more second species bound onto said metal layer, wherein each of said one or more first species is a molecule having a structural formula $X_1$—$(CH_2)_c$—$O$—$([CH_2]_t$—$CH_2$—$O)_n$—$R_1$—$S$-$M$ and each of said one or more second species is a molecule $Y_1$—$([CH_2]_t$—$CH_2$—$O)_n$—$R_3$—$S$-$M$ wherein:
$Y_2$ is either H or —$S$—$R_4$—$(O$—$CH_2$—$[CH_2]_t)_n$—$Y_1'$,
$R_1$, $R_3$ and $R_4$ are each independently a saturated or ethylenically unsaturated hydrocarbyl group with 3 to 30 carbon atoms selected from the group consisting of alkyl, alkenyl, cycloalkyl, cycloalkylalkyl, cycloalkenyl, cycloalkenylalkyl and cycloalkylalkenyl, said group optionally comprising one or more heteroatoms selected from nitrogen, oxygen and sulfur in the main chain, and said group optionally comprising one or more oxo substituents,
$Y_1$ and $Y_1'$ are independently either a hydroxy group or a methoxy group,
M is said metal layer to which said one or more molecules are bounded,
t is an integer from 1 to 2,
n is an integer from 3 to 15,000,
c is an integer from 0 to 3,
$X_1$ is selected from the group consisting of fluorophenyl, fluorobenzoyl, fluorophenoxycarbonyl, nitrophenoxycarbonyl, oxiranyl, aziridinyl, $C_{2-12}$ alkenyl, imino-ether, dichlorotriazinyl, sulfonyl halide, alkoxycarbonyl, isothiocyanato, isocyanato, carbonyl halide, haloalkylcarbonyl, carboxylic acid anhydride, diazonium carbonyl, N-(2-oxotetrahydro-3-thienyl) amido and N-carboxy-thiazolidinyl-2-thione.

Preferably, a treatment to remove any metal oxide layer present at the surface of the metal layer is performed according to any method well known by the person skilled in the art.

In a fifth aspect, a sensor is provided for the detection of an analyte in a sample fluid, the device comprising:
a device according to the second aspect on which at least one biomolecule is immobilized by a covalent bound, and
a transducer.

Figure 3:
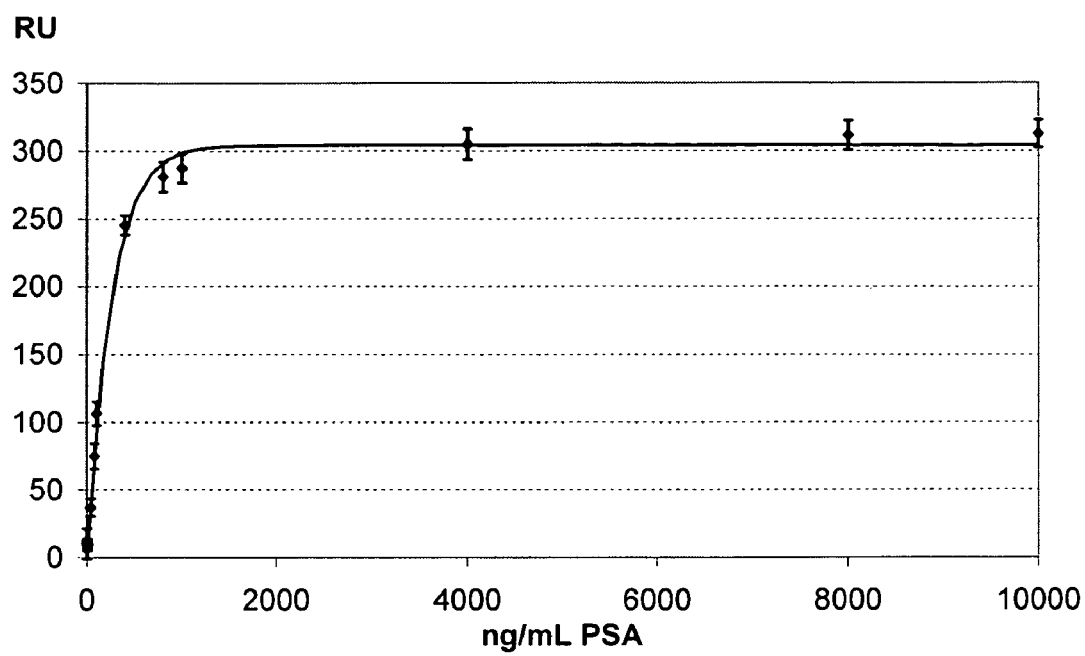
FIG. 3 shows a surface plasmon resonance (SPR) signal recorded by a sensor according to an embodiment.

FIG. 3 shows the surface plasmon resonance (SPR) signal obtained for various concentrations of a prostate specific antigen (PSA) put in presence of an anti-PSA antibody immobilized on a gold surface via covalent bonding with a mono-layer of species obtained from Example 8. The binding signals are expressed in resonance units (RU).

Figure 4:
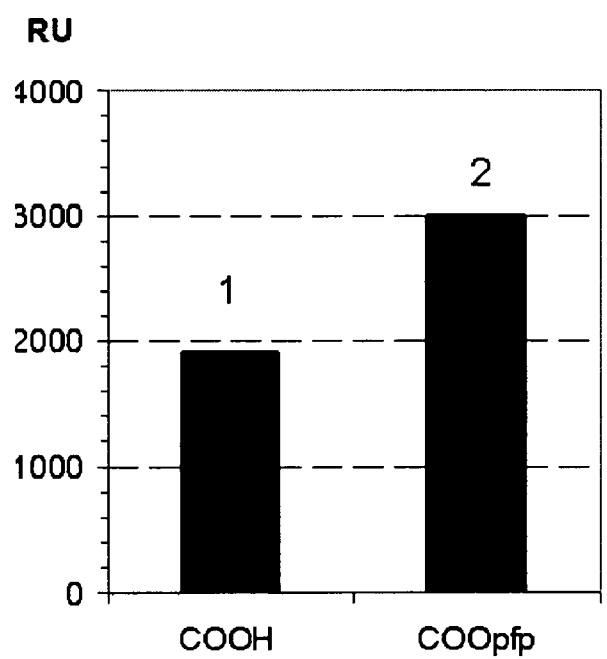
FIG. 4 shows SPR data comparing the efficiency of binding of an anti-body to a device according to a preferred embodiment and to a device according to the prior art.

FIG. 4 shows comparative SPR data for the immobilization of anti-PSA antibody on [1] a self-assembled monolayer of the prior art activated via an activation step with a carbodiimide followed by a pentafluorophenol binding and [2] on a self-assembled monolayer according to Example 8. The binding signal is expressed in resonance units (RU) and this signal is clearly higher in the case of the exemplary embodiment. In a sixth aspect, a method for manufacturing a sensor according to the fifth aspect is provided, wherein the method comprises the steps of:
contacting a device according to the second aspect with a solution of at least one biomolecule,
connecting said device to a transducer.

In an embodiment of this sixth aspect, the at least one biomolecule has at least one primary amino group. In another embodiment of this sixth aspect, the device and/or said at least one biomolecule is not chemically activated prior to contacting.

EXAMPLE 1

Synthesis of 2-{2-[2-(11-mercapto-undecyloxy) ethoxy]ethoxy}ethyl 2,3,4,5,6-pentafluorobenzoate and Analogues Derived from Higher Polyethylene Glycols 2-{2-[2-(11-mercapto-undecyloxy)ethoxy]ethoxy}ethyl-2,3,4,5,6-pentafluoro benzoate is an example of a compound (shown schematically below) of the general formula $X_1$—$(CH_2)_c$—$O$—$([CH_2]_t$—$CH_2)_n$—$O$—$R_1$—$S$—$X_2$ wherein $X_1$=fluorobenzoyl, t=1, c=0 and n=3.

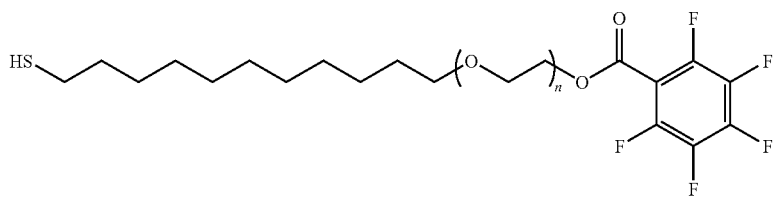

The present molecule has been synthesized according to the following synthesis scheme:

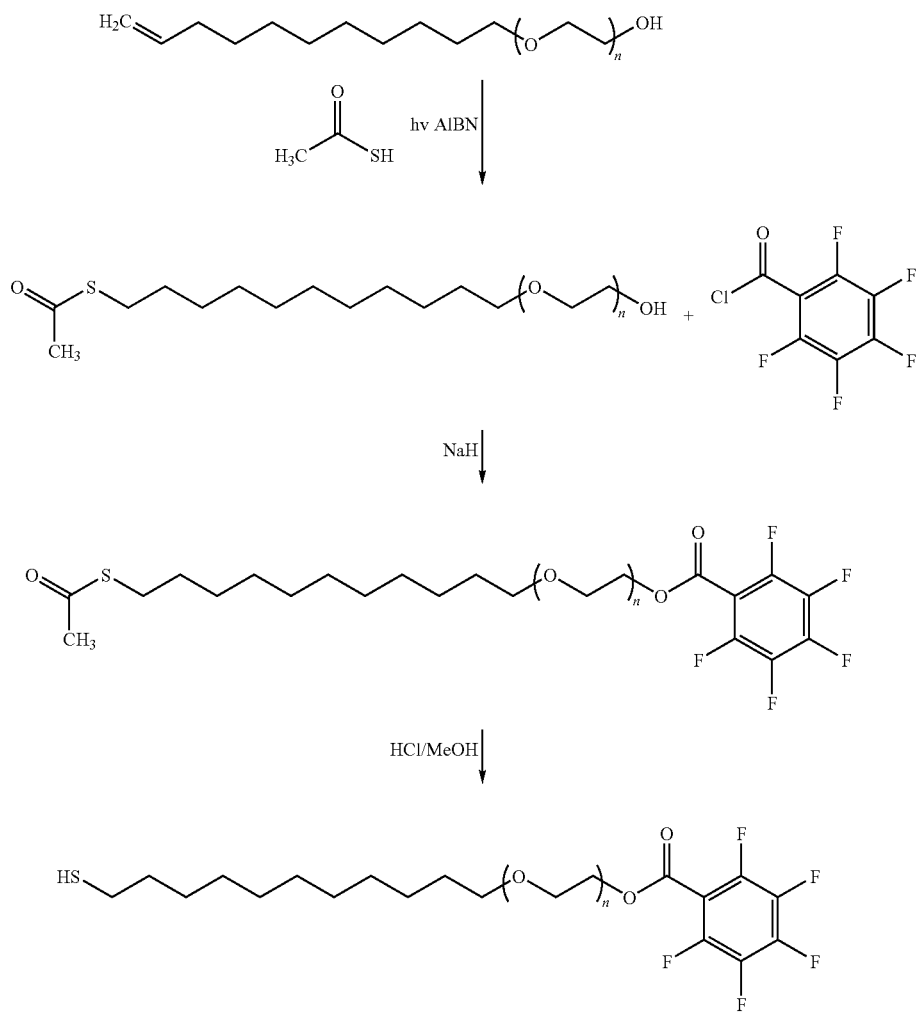

A solution of 2-{2-[2-(undec-10-enyloxy)ethoxy]ethoxy}ethanol (n=3) (commercially available at Prochimia) in ethanol containing 4 molar equivalents of thioacetic acid and 10 mg of AIBN was irradiated under UV light for 6 hours under an atmosphere of nitrogen. The reaction mixture was concentrated by rotary evaporation at reduced pressure and purification by chromatography on silica gel.

A mixture of NaH and the thioacetate in THF/DMF was stirred for about 1 hour under an atmosphere of argon, and then pentafluorobenzoyl chloride was added. After 36 hours, the reaction mixture was concentrated by rotary evaporation at reduced pressure and extracted with dichloromethane and water. The organic portion was dried over $MgSO_4$ and concentrated by rotary evaporation at reduced pressure. The product was purified by chromatography on silica gel.

A solution of the thioacetate in 0.1M HCl in MeOH was deprotected under an atmosphere of nitrogen by refluxing for about 4 h. The reaction mixture was concentrated by rotary evaporation at reduced pressure and purification by chromatography on silica gel.

The above synthetic procedure can be executed with n taking any value from 3 to 15,000 provided that a suitable oligo- or poly-ethylene glycol derivative is used instead of 2-{2-[2-(undec-10-enyloxy)ethoxy]ethoxy}ethanol. If necessary, type and/or amount of solvent and/or reaction time may be adapted in view of n, especially accounting for the physical state (liquid or solid) and the solubility of the polyethyleneglycol involved.

EXAMPLE 2

Synthesis of 2-(2-{2-[2-(11-mercapto-undecyloxy)ethoxy]ethoxy}ethoxy)methyl pentafluorophenoxycarbonyl (n=3) and Analogues Derived from Higher Polyethylene Glycols 2-(2-{2-[2-(11-mercapto-undecyloxy)ethoxy]ethoxy}ethoxy)methyl pentafluorophenoxycarbonyl is an example of a compound (shown schematically below) of the general formula $X_1$—$(CH_2)_c$—O—$([CH_2]_t$—$CH_2)_n$—O—$R_1$—S—$X_2$ wherein $X_1$=pentafluorophenoxycarbonyl, c=1 and n=3.

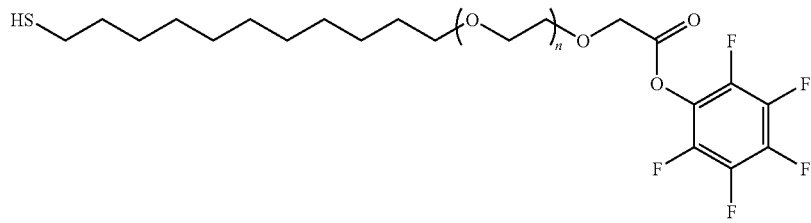
The present molecule has been synthesized according to the following synthesis scheme:
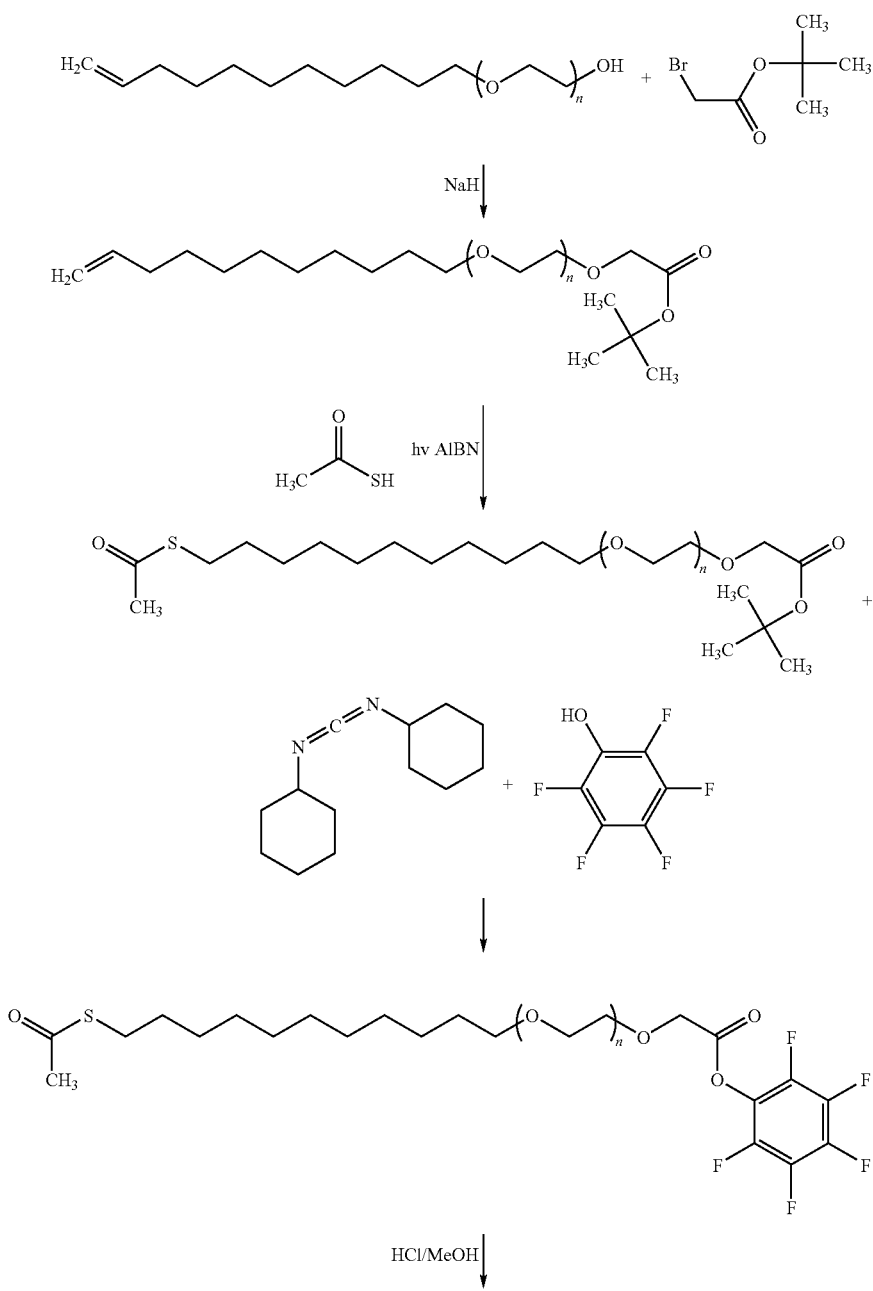

-continued

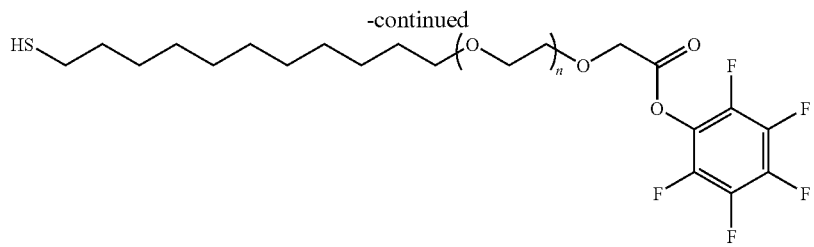

NaH was added to a DMF/THF solution of 2-{2-[2-(undec-10-enyloxy)ethoxy]ethoxy}ethanol (n=3) (commercially available from Prochimia). The mixture was stirred for about 10 min. and tert-butyl bromoacetate was added dropwise. The mixture was stirred at RT overnight and was concentrated by rotary evaporation at reduced pressure and extracted with ethyl acetate and water. The reaction mixture was concentrated by rotary evaporation at reduced pressure and purification by chromatography on silica gel.

To a solution of the tert-butyl acetate derivative in toluene was added thioacetic acid and AIBN. The mixture was irradiated under UV light for 6 hours under an atmosphere of nitrogen. The reaction mixture was concentrated by rotary evaporation at reduced pressure and purification by chromatography on silica gel.

A solution of the thioacetate in DMF was activated with dicyclohexyl-carbodiimide under an atmosphere of nitrogen by stirring at room temperature for about 12 hours and then pentafluorophenol was added. The reaction mixture was stirred at room temperature and extracted with water. The reaction mixture was concentrated by rotary evaporation at reduced pressure and purification by chromatography on silica gel.

A solution of the thioacetate in 0.1M HCl in MeOH was deprotected under an atmosphere of nitrogen by refluxing for about 4 hours. The reaction mixture was concentrated by rotary evaporation at reduced pressure and purification by chromatography on silica gel.

The above synthetic procedure can be executed with n taking any value from 3 to 15,000 provided that a suitable oligo- or poly-ethylene glycol derivative is used instead of 2-{2-[2-(undec-10-enyloxy)ethoxy]ethoxy}ethanol. If necessary, type and/or amount of solvent and/or reaction time may be adapted in view of n, especially accounting for the physical state (liquid or solid) and the solubility of the polyethyleneglycol involved.

EXAMPLE 3

Synthesis of 2-{2-[2-(11-mercapto-undecyloxy)ethoxy]ethoxy}ethoxy chloridocarbonyl (n=3) and Analogues Derived from Higher Polyethylene Glycols 2-{2-[2-(11-mercapto-undecyloxy)ethoxy]ethoxy}ethoxy chloridocarbonyl is an example of a compound (shown schematically below) of the general formula $X_1$—$(CH_2)_c$—O—$([CH_2]_t$—$CH_2$—$O)_n$—$R_1$—S—$X_2$ wherein $X_1$=carbonyl chloride, c=0 and, $X_2$=H, $R_1$=$(CH_2)_{11}$.

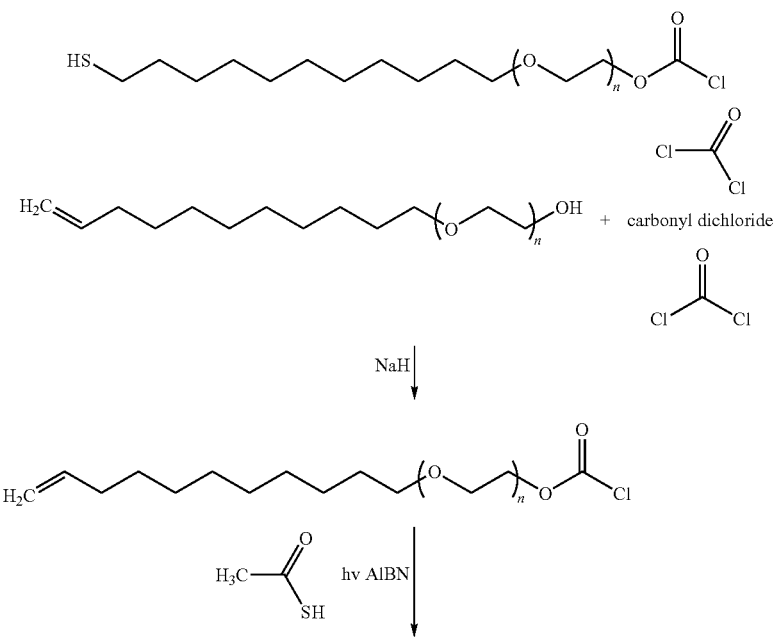

-continued

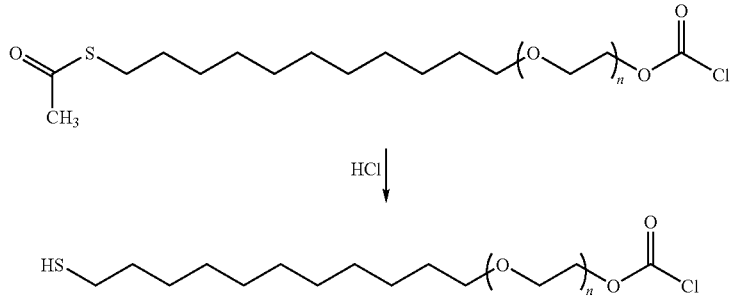

A mixture of 1.5 molar equivalent NaH and 1 molar equivalent 2-{2-[2-(undec-10-enyloxy)ethoxy]ethoxy}ethanol (n=3) (commercially available at Prochimia) in 50 ml DMF was stirred for about 30 minutes under an atmosphere of argon, and then 1.5 molar equivalent of carbonyl dichloride was added. Next, the solution was stirred for 24 hours under an atmosphere of argon, followed by quenching with 25 ml methanol. The reaction mixture was then extracted with diethyl ether and water. The organic portion was dried over $MgSO_4$ and concentrated by rotary evaporation at reduced pressure. The product was purified by chromatography on silica gel.

A solution of this product (1 molar equivalent) in methanol containing 4 molar equivalents of thioacetic acid and 10 mg of 2,2'-azobis(isobutyronitrile) (AIBN) were irradiated under UV light for 24 hours under an atmosphere of argon. The reaction mixture was concentrated by rotary evaporation at reduced pressure and purification by chromatography on silica gel.

A solution of the thioacetate (1 molar equivalent) in a solution containing 1M HCl and MeOH (1/1) was deprotected under an atmosphere of nitrogen by stirring the reaction for 24 hours. The solution was then extracted with an organic solvent and $H_2O$, followed by drying of the organic phase on $MgSO_4$. The reaction mixture was concentrated by rotary evaporation at reduced pressure and purification by chromatography on silica gel. Next, the product was again concentrated using rotary evaporation.

The above synthetic procedure can be executed with n taking any value from 3 to 15,000 provided that a suitable oligo- or poly-ethylene glycol derivative is used instead of 2-{2-[2-(undec-10-enyloxy)ethoxy]ethoxy}ethanol. If necessary, type and/or amount of solvent and/or reaction time may be adapted in view of n, especially accounting for the physical state (liquid or solid) and the solubility of the polyethyleneglycol involved.

EXAMPLE 4

Synthesis of 1-chloro-3-(2-[2-(2-(11-mercaptoundecyloxy)-ethoxy)ethoxy]ethoxy)propan-2-one and Analogues Derived from Higher Polyethylene Glycols 1-chloro-3-(2-[2-(2-(11-mercaptoundecyloxy)-ethoxy)ethoxy]ethoxy)propan-2-one is an example of a compound (shown schematically below) of the general formula $X_1$—$(CH_2)_c$—O—$([CH_2]_t$—$CH_2$—$O)_n$—$R_1$—S—$X_2$ wherein $X_1$=chloroalkylcarbonyl, c=1 and n=3, t=1, $X_2$=H, $R_1$=$(CH_2)_{11}$.

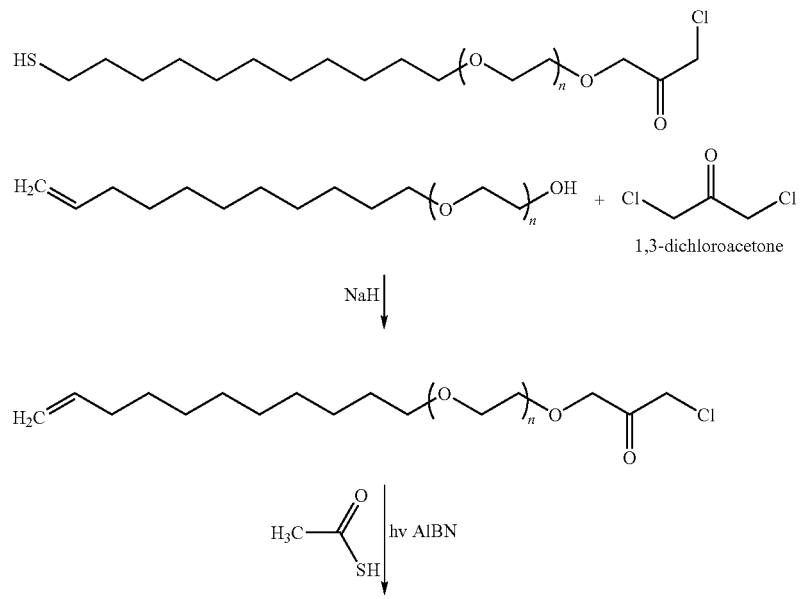

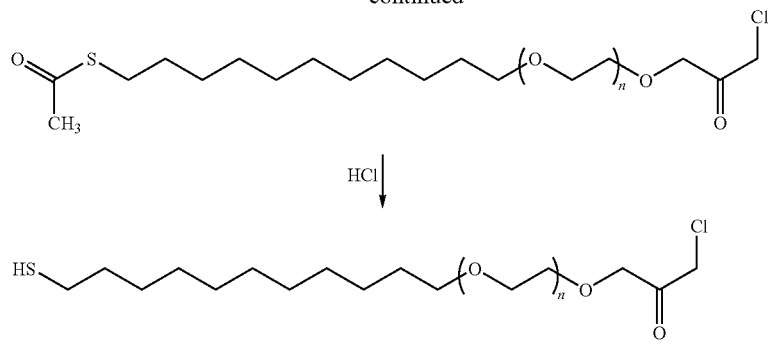

A mixture of 1.5 molar equivalent NaH and 1 molar equivalent 2-{2-[2-(undec-10-enyloxy)ethoxy]ethoxy}ethanol (n=3) (commercially available at Prochimia) in 50 ml DMF was stirred for about 30 minutes under an atmosphere of argon, and then 1.5 molar equivalent of 1,3-dichloroacetone was added. Next, the solution was stirred for 24 hours under an atmosphere of argon, followed by quenching with 25 ml methanol. The reaction mixture was then extracted with diethyl ether and water. The organic portion was dried over $MgSO_4$ and concentrated by rotary evaporation at reduced pressure. The product was purified by chromatography on silica gel.

A solution of this product (1 molar equivalent) in methanol containing 4 molar equivalents of thioacetic acid and 10 mg of 2,2'-azobis(isobutyronitrile) AIBN were irradiated under UV light for 24 hours under an atmosphere of argon. The reaction mixture was concentrated by rotary evaporation at reduced pressure and purification by chromatography on silica gel.

A solution of the thioacetate (1 molar equivalent) in a solution containing 1M HCl and MeOH (1/1) was deprotected under an atmosphere of nitrogen by stirring the reaction for 24 hours. The solution was then extracted with an organic solvent and $H_2O$, followed by drying of the organic phase on $MgSO_4$. The reaction mixture was concentrated by rotary evaporation at reduced pressure and purification by chromatography on silica gel. Next, the product was again concentrated using rotary evaporation.

The above synthetic procedure can be executed with n taking any value from 3 to 15,000 provided that a suitable oligo- or poly-ethylene glycol derivative is used instead of 2-{2-[2-(undec-10-enyloxy)ethoxy]ethoxy}ethanol. If necessary, type and/or amount of solvent and/or reaction time may be adapted in view of n, especially accounting for the physical state (liquid or solid) and the solubility of the polyethyleneglycol involved.

EXAMPLE 5

Synthesis of 11-(2-(2-(2-(oxiran-2-ylmethoxy)ethoxy)ethoxy)-ethoxy)undecane-1-thiol and Analogues Derived from Higher Polyethylene Glycols 11-(2-(2-(2-(oxiran-2-ylmethoxy)ethoxy)ethoxy)-ethoxy)undecane-1-thinly is an example of a compound (shown schematically below) of the general formula $X_1$—$(CH_2)_c$—O—$([CH_2]_t$—$CH_2$—$O)_n$—$R_1$—S—$X_2$ wherein $X_1$=oxiranyl, c=1 and n=3, t=1, $X_2$=H, $R_1$=$(CH_2)_{11}$.

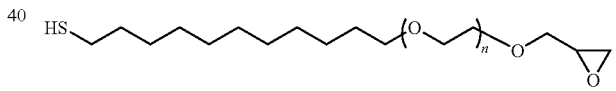

This molecule has been synthesized according to the following synthesis scheme:

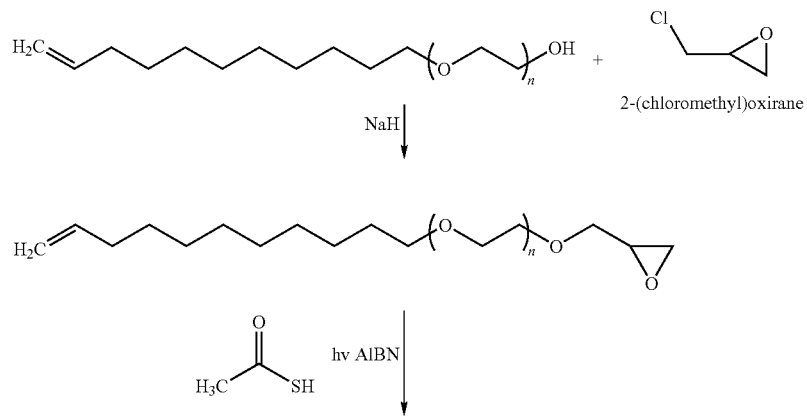

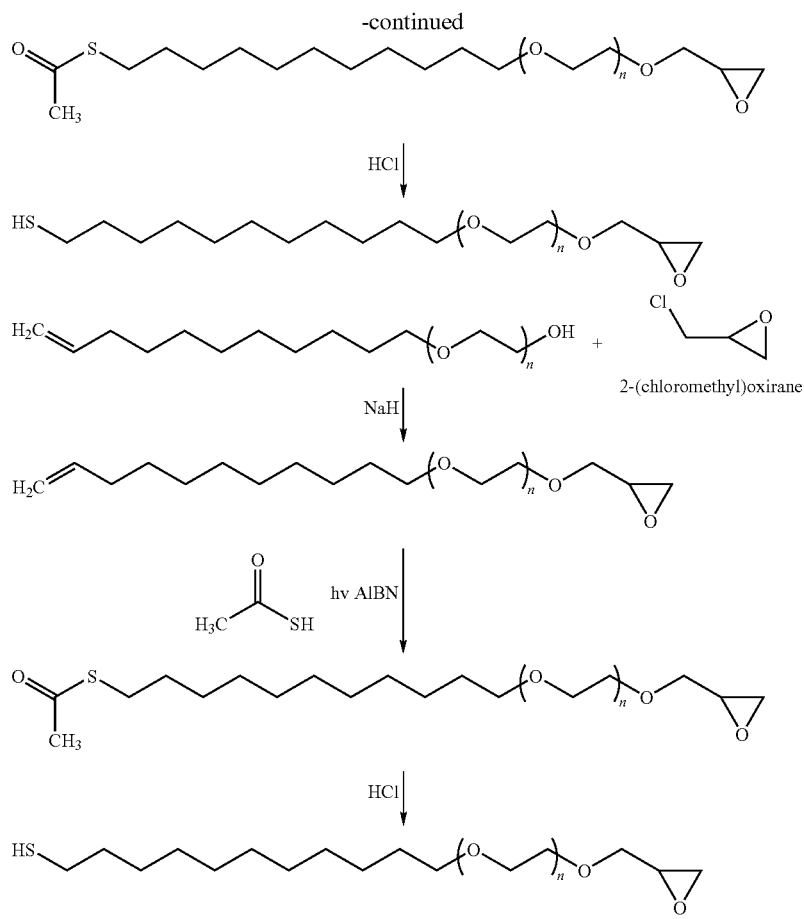

A mixture of 1.5 molar equivalent NaH and 1 molar equivalent 2-{2-[2-(undec-10-enyloxy)ethoxy]ethoxy}ethanol (n=3) (commercially available at Prochimia) in 50 ml DMF was stirred for about 30 minutes under an atmosphere of argon, and then 1.5 molar equivalent of 2-(chloromethyl) oxirane was added. Next, the solution was stirred for 24 hours under an atmosphere of argon, followed by quenching with 25 ml methanol. The reaction mixture was then extracted with diethyl ether and water. The organic portion was dried over $MgSO_4$ and concentrated by rotary evaporation at reduced pressure. The product was purified by chromatography on silica gel.

A solution of this product (1 molar equivalent) in methanol containing 4 molar equivalents of thioacetic acid and 10 mg of 2,2'-azobis(isobutyronitrile) (AIBN) were irradiated under UV light for 24 hours under an atmosphere of argon. The reaction mixture was concentrated by rotary evaporation at reduced pressure and purification by chromatography on silica gel.

A solution of the thioacetate (1 molar equivalent) in a solution containing 1M HCl and MeOH (1/1) was deprotected under an atmosphere of nitrogen by stirring the reaction for 24 hours. The solution was then extracted with an organic solvent and $H_2O$, followed by drying of the organic phase on $MgSO_4$. The reaction mixture was concentrated by rotary evaporation at reduced pressure and purification by chromatography on silica gel. Next, the product was again concentrated using rotary evaporation.

The above synthetic procedure can be executed with n taking any value from 3 to 15,000 provided that a suitable oligo- or poly-ethylene glycol derivative is used instead of 2-{2-[2-(undec-10-enyloxy)ethoxy]ethoxy}ethanol. If necessary, type and/or amount of solvent and/or reaction time may be adapted in view of n, especially accounting for the physical state (liquid or solid) and the solubility of the polyethyleneglycol involved.

EXAMPLE 6

Synthesis of 2-(2-(2-(11-mercaptoundecyloxy) ethoxy)-ethoxy)ethoxy acetylchloride and Analogues Derived from Higher Polyethylene Glycols 2-(2-(2-(1-mercaptoundecyloxy)ethoxy)-ethoxy)ethoxy acetylchloride is an example of a compound (shown schematically below) of the general formula $X_1$—$(CH_2)_c$—O—$([CH_2]_t$—$CH_2$—$O)_n$—$R_1$—S—$X_2$ wherein $X_1$=carbonyl chloride, c=1 and n=3, t=1, $X_2$=H, $R_1$=$(CH_2)_{11}$.

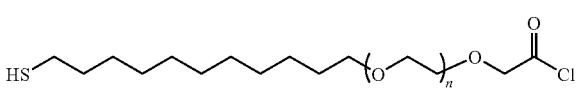

The present molecule has been synthesized according to the following synthesis scheme:

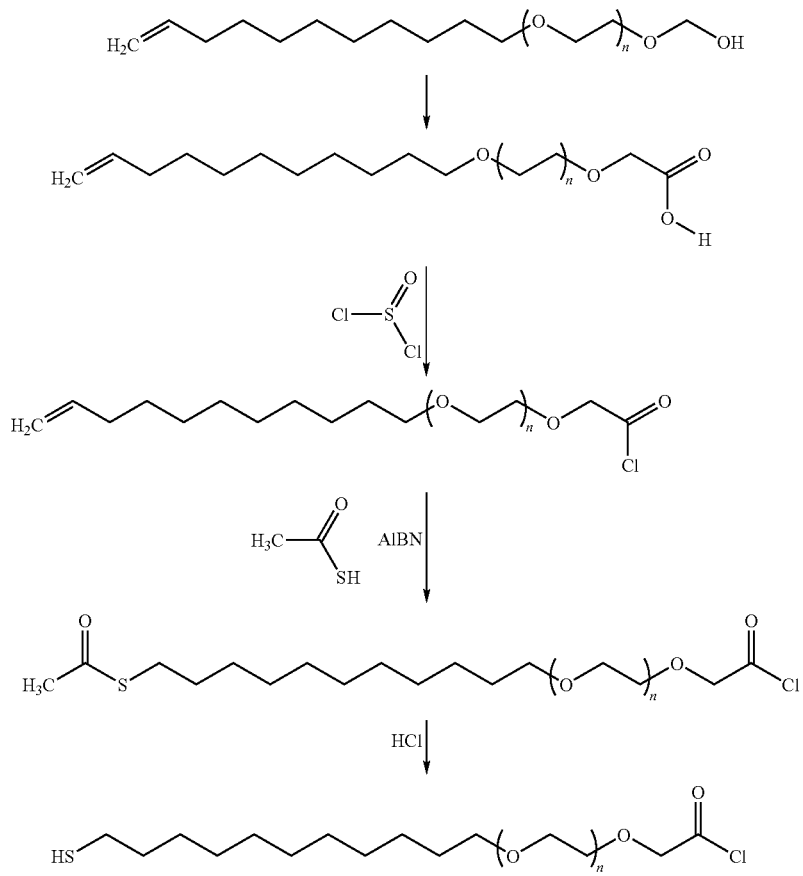

NaH (1.5 molar equivalent) was added to a 50 ml DMF solution of 1 molar equivalent of 2-{2-[2-(undec-10-enyloxy)ethoxy]ethoxy}ethanol (n=3). The mixture was stirred for about 30 minutes and tert-butyl bromoacetate (1.5 molar equivalent) was added dropwise. The mixture was stirred at room temperature for 24 hours under an atmosphere of argon. The product was quenched with 25 ml of methanol. The reaction mixture was then extracted with diethyl ether and water. The organic portion was dried over $MgSO_4$ and concentrated by rotary evaporation at reduced pressure. The product was purified by chromatography on silica gel. The resulting product was concentrated using rotary evaporation. The olefin was deprotected in a mixture of (1/1) HCl and $H_2O$ under an atmosphere of nitrogen. The reaction mixture was then concentrated by rotary evaporation at reduced pressure and extracted with dichloromethane and water. The organic portion was dried over $MgSO_4$ and concentrated by rotary evaporation at reduced pressure. The product was purified by chromatography on silica gel.

In an Erlenmeyer flask fitted by a ground-glass joint to a reflux condenser capped with a calcium chloride drying tube, 2-(2-(2-undec-10-enyloxy-ethoxy)-ethoxy)-acetic acid (n=3) (1 molar equivalent) and thionyl chloride (1.2 molar equivalents) were placed. The flask was warmed for 3 days in a heating bath kept at 45-50° C. Finally the mixture was heated at 60° C. for 5 hours. After cooling, it was transferred to a modified Claisen flask and distilled at reduced pressure. A calcium chloride guard tube was inserted between the vacuum line and the apparatus, and the flask was heated with a bath.

A solution of the olefin (1 molar equivalent) in methanol containing 4 molar equivalents of thioacetic acid and 10 mg of AIBN were irradiated under UV light for 24 hours under an atmosphere of argon. The product was purified by filtering on a glass filter followed by rotary evaporation at reduced pressure and purification by chromatography on silica gel.

A solution of the thioacetate (1 molar equivalent) in a solution containing 1M HCl and MeOH (1/1) was deprotected under an atmosphere of nitrogen by stirring the reaction for 24 hours. The solution was then extracted with an organic solvent and $H_2O$, followed by drying of the organic phase on $MgSO_4$. The reaction mixture was concentrated by rotary evaporation at reduced pressure and purification by chromatography on silica gel. Next, the product was again concentrated using rotary evaporation.

The above synthetic procedure can be executed with n taking any value from 3 to 15,000 provided that a suitable oligo- or poly-ethylene glycol derivative is used instead of 2-{2-[2-(undec-10-enyloxy)ethoxy]ethoxy}ethanol. If necessary, type and/or amount of solvent and/or reaction time may be adapted in view of n, especially accounting for the physical state (liquid or solid) and the solubility of the polyethyleneglycol involved.

EXAMPLE 7

Synthesis of 2-{2-[2-(2-{2-[2-(11-mercapto-undecyloxy)ethoxy]ethoxy}ethoxy)ethoxy]ethoxy}ethyl 2,3,4,5,6-pentafluoro-benzoate and Analogues Derived from higher Polyethylene Glycols 2-{2-[2-(2-{2-[2-(11-mercapto-undecyloxy)ethoxy]ethoxy}ethoxy)ethoxy]-ethoxy}ethyl 2,3,4,5,6-pentafluorobenzoate is an example of a compound of the general formula $X_1-(CH_2)_c-O-([CH_2]_t-CH_2-O)_n-R_1-S-X_2$ wherein $X_1$=fluorobenzoyl, $X_2$=H, c=0, t=1, n=6, and $R_1$=$(CH_2)_{11}$. The present molecule has been synthesized according to the following synthesis scheme in three steps:

In a first step, in a dry bottle comprising a magnetic stirrer and under argon atmosphere, 0.0058 mole of 2-[2-(2-{2-[2-(undec-10-enyloxy)ethoxy]ethoxy}ethoxy)ethoxy]ethoxy}ethanol was dissolved in a sufficient amount of ethanol. 0.023 mole of thioacetic acid and 10 mg of 2,2'-azobisisobutyronitrile (AIBN) were added and the solution was irradiated with UV light for 24 hours under an atmosphere of argon. The product was purified by filtering on a glass filter followed by rotary evaporation at reduced pressure and by purification on a silica column using ethyl acetate/methanol (95/5). The product was obtained in 89% yield and was characterized as follows: $^1$H NMR (300MHz, CDCl$_3$): δ 3.65 (20H, m), δ 3.45 (2H, t), δ 2.85 (2H, t), δ 2.5 (1H, s), δ 2.30 (3H, s), and 1.65-1.23 (18H, m).

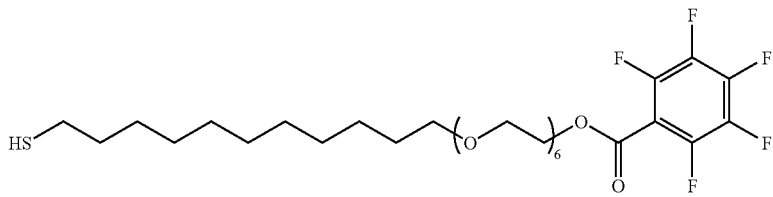

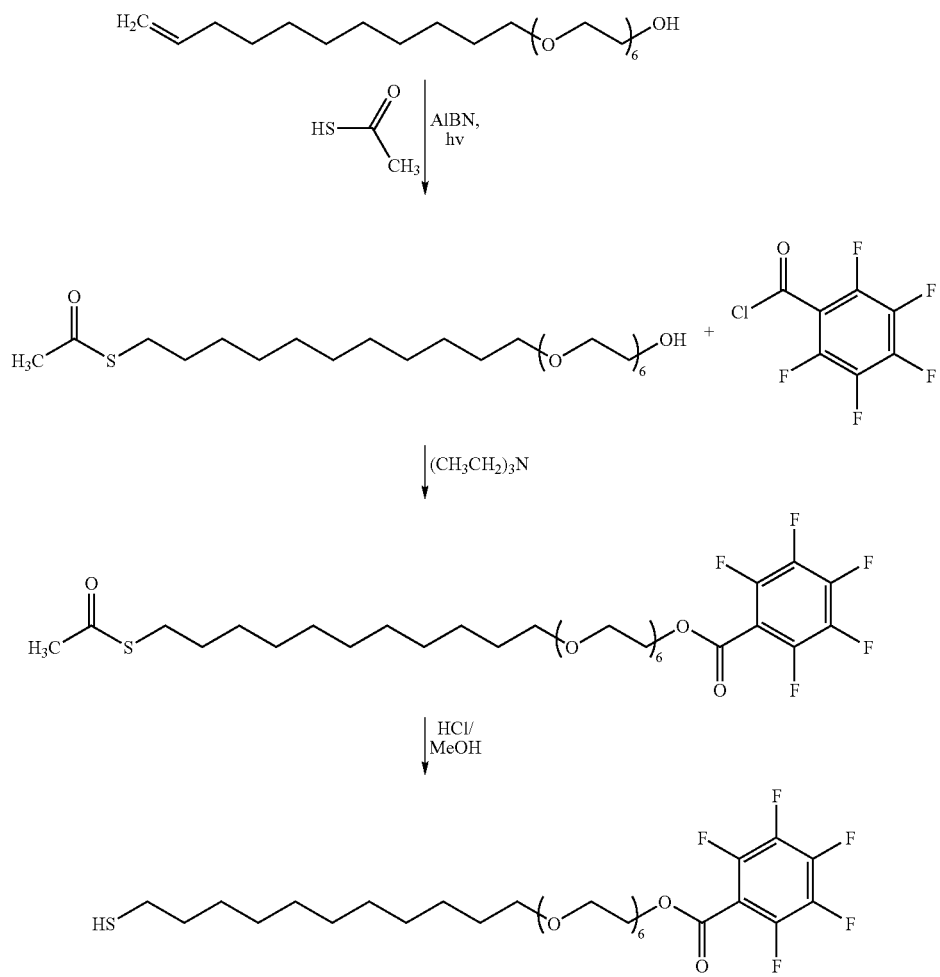

In a second step, in a dry bottle having a magnetic stirrer and under argon atmosphere, 0.0052 mole of the product obtained in step 1 was dissolved in a sufficient amount of $CH_2Cl_2$. 0.00785 mole of triethylamine was added and the solution was stirred for 1 hour under an atmosphere of argon. 0.00785 mole of pentafluorobenzoyl chloride was then added and the solution was stirred for 24 hours under an atmosphere of argon. The product was purified by rotary evaporation at reduced pressure and by purification on a silica column using ethyl acetate/methanol (95/5). The product was obtained in 80% yield and was characterized as follows: $^1$H NMR (300MHz, CDCl$_3$): δ 4.53 (2H, t), δ 3.82 (2H, t), δ 3.65 (20H, m), δ 3.45 (2H, t), δ 2.85 (2H, t), δ 2.30 (3H, s), and 1.65-1.23 (18H, m).

In a third step, in a dry bottle having a magnetic stirrer and under argon atmosphere, 0.00248 mole of the product obtained in step 2 was dissolved in an excess amount of solution containing 1M HCl and EtOH (1/1). The solution was stirred for 24 hours. The solution was then extracted with diethyl ether and $H_2O$. The organic phase was dried on MgSO$_4$. The product was then concentrated using rotary evaporation. Next, the product was purified on a silica column using ethyl acetate. The product was again concentrated using rotary evaporation. The product was obtained in 56% yield and was characterized as follows:

1H NMR (300MHz, CDCl3): δ 4.53 (2H, t), δ 3.82 (2H, t), δ 3.65 (20H, m), δ 3.45 (2H, t), δ 2.51 (2H, q), 1.60-1.27 (18H, m), and C13 NMR (300MHz, CDCl$_3$): 159.27; 148.61; 143.98; 139.89; 136.54; 108.31; 70.93; 70.38; 69.0; 66.09; 34.38; 29.96; 29.81; 29.38; 28.68; 26.42; and 24.93 ppm.

The above synthetic procedure can be executed with n taking any value from 3 to 15,000 provided that a suitable oligo- or poly-ethylene glycol derivative is used instead of 2-[2-(2-{2-{2-[2-(undec-10-enyloxy)ethoxy]ethoxy}ethoxy)ethoxy]ethoxy}ethanol. If necessary, type and/or amount of solvent and/or reaction time may be adapted in view of n, especially accounting for the physical state (liquid or solid) and the solubility of the polyethyleneglycol involved.

EXAMPLE 8

Synthesis of 2-(2-{2-[2-(2-{2-[2-(11-mercaptoyldis-ulfanyl-undecyloxy)ethoxy]ethoxy}ethoxy)ethoxy] ethoxy}acetic acid pentafluorophenyl ester and Analogues Derived from Higher Polyethylene Glycols

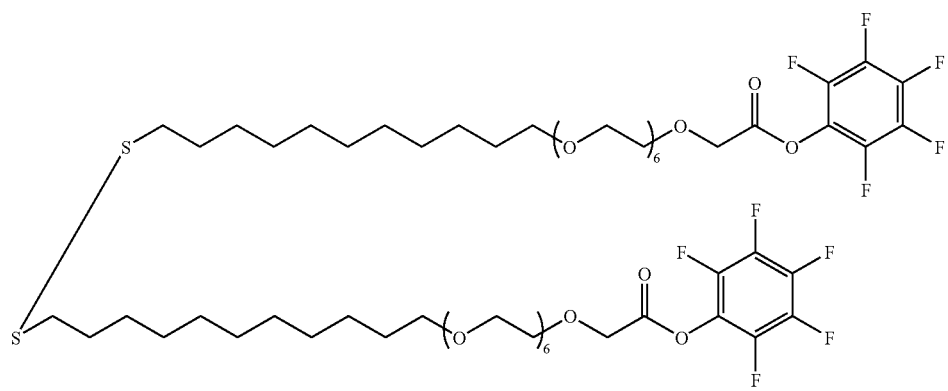

2-(2-{2-[2-(2-{2-[2-(11-mercapto-undecyloxy)ethoxy] ethoxy}ethoxy)ethoxy]-ethoxy}ethoxy)methyl pentafluorophenoxycarbonyl is an example of a compound of the general formula $X_1—(CH_2)_c—O—([CH_2]_t—CH_2—O)_n—R_1—S—X_2$ wherein $X_1$=pentafluorophenoxycarbonyl, $X_2$=$X_1$—$(CH_2)_c$—O—$([CH_2]_t$—$CH_2$—O$)_n$—$R_1$—S, c=1, t=1, n=6, and $R_1$=$(CH_2)_{11}$, which has been synthesized according to the following scheme:

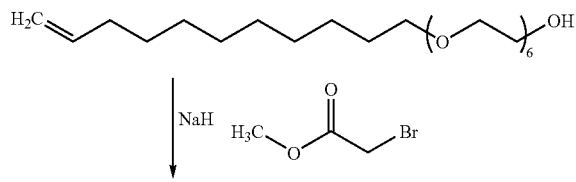

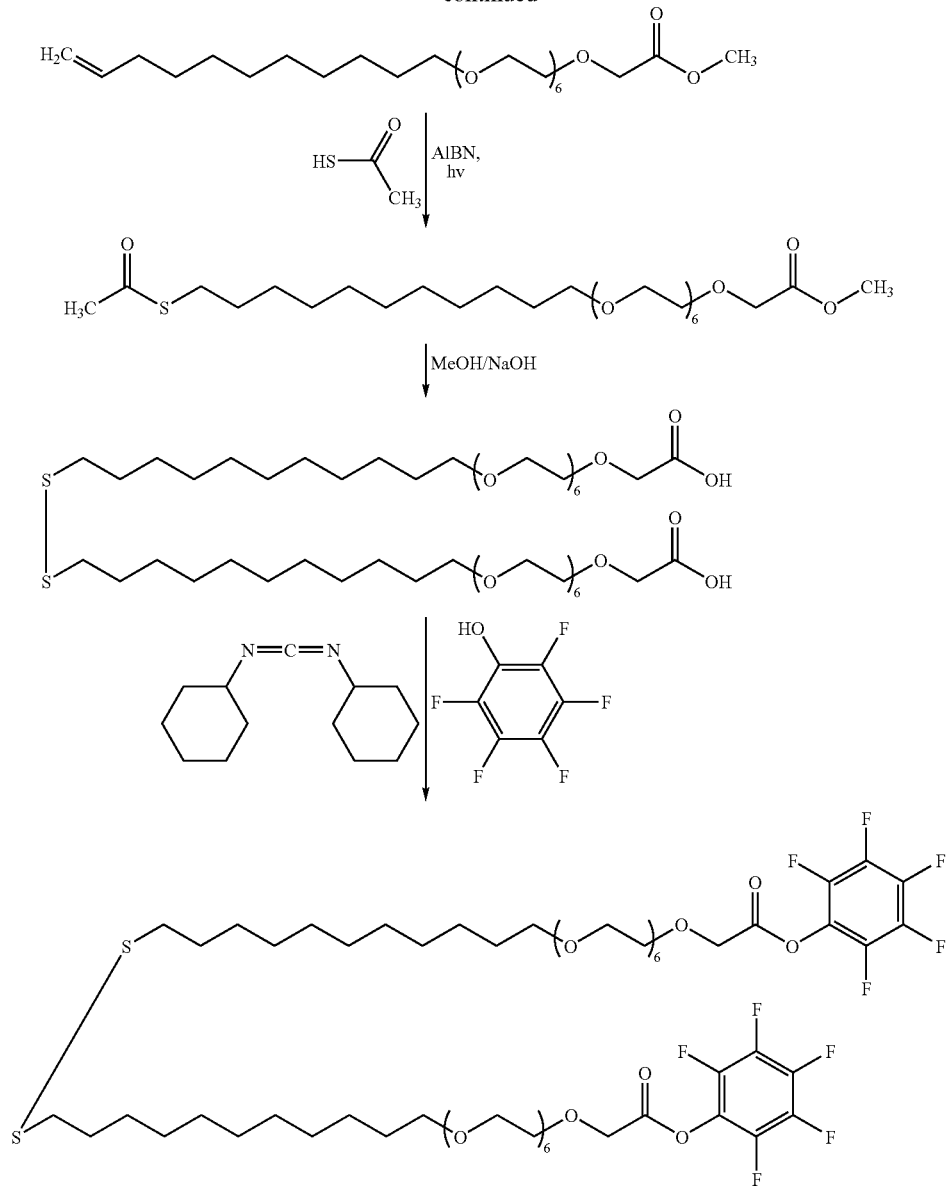

In a first step, in a dry bottle comprising a magnetic stirrer and under argon atmosphere, 9.2 mmole of 2-[2-(2-{2-{2-[2-(undec-10-enyloxy)ethoxy]ethoxy}ethoxy}ethoxy)ethoxy]ethoxy}ethanol and 13.8 mmole of NaH were dissolved in 50 mL DMF. The solution was stirred for 30 minutes. 13.8 mmole of methyl bromo-acetate was added and the solution was stirred for 24 hours under an atmosphere of argon. The product was quenched with 25 mL of methanol. The solution was then extracted with diethyl ether and $H_2O$. The organic phase was dried on $MgSO_4$. The product was then concentrated using rotary evaporation. Next, the product was purified on a silica column using ethylacetate. The product was again concentrated using rotary evaporation. The product was obtained in 50% yield and was characterized as follows: 1H NMR (300MHz, $CDCl_3$): δ 5.82 (1H, m), δ 4.98 (2H, m), δ 4.18 (2H, s), δ 3.75 (3H, s), δ 3.65 (24H, m), δ 3.41 (2H, t), and 1.65-1.23 (18H, m).

In a second step, in a dry bottle comprising a magnetic stirrer and under argon atmosphere, 1.2 mmole of the product obtained in step 2 was dissolved in a sufficient amount of methanol. 4.6 mmole of thioacetic acid and 10 mg of 2,2'-azobis-isobutyronitrile (AIBN) were added and the solution was irradiated with UV light for 24 hours under an atmosphere of argon. The product was purified by filtering on a glass filter followed by rotary evaporation at reduced pressure and by purification on a silica column using ethyl acetate/methanol (95/5). The product was obtained in 83% yield and was characterized as follows: 1H NMR (300MHz, $CDCl_3$): δ 4.18 (2H, s), δ 3.75 (3H, s), δ 3.65 (22H, m), δ 3.45 (2H, t), δ 2.85 (2H, t), δ 2.33 (3H, s), and 1.65-1.23 (18H, m).

In a third step, in a dry bottle comprising a magnetic stirrer, 1 molar equivalent (0.2 g) of the product obtained in step 2 was dissolved in a solution containing methanol/1M NaOH (3/1) (15 mU 5 mL). The solution was stirred for 24 hours. HCl was added to acidify the solution. The solution was then extracted with CH$_2$Cl$_2$ and H$_2$O. The organic phase was dried on MgSO4. The product is then concentrated using rotary evaporation. Yield: 98%. 1H NMR (300MHz, CDCl$_3$): δ 4.18 (4H, s), δ 3.65 (41H, m), δ 3.45 (4H, t), δ 2.65 (4H, t), 1.65-1.23 (36H, m).

In a fourth step, in a dry bottle comprising a magnetic stirrer and under argon atmosphere, 9.5 10$^{-5}$. mole of the product obtained in step 3 and 1.14 10$^{-4}$ mole pentafluorophenol (PFP) was dissolved in dry ethyl acetate (100 mL). The solution was stirred and cooled down to 0° C. 1.14 10$^{-4}$ mole dicyclohexyl-carbodiimide (DCC) was added and the solution was stirred for 30 minutes. Next, the solution was stirred for 3 days at room temperature. The product was concentrated by rotary evaporation at reduced pressure. The product was obtained in 84% yield and was characterized as follows:

1H NMR (300MHz, CDCl3): δ 4.56 (4H, s), δ 4.5-3.73 (48H, m), δ 3.45 (4H, t), δ 2.69 (4H, t), δ 1.75-1.28 (58H, m) (36H, m+22H),

C13 (300MHz, CDCl3): 166.61; 157.13; 142.27; 139.18; 136.66; 131.95; 71.53; 70.58; 68.97; 67.87; 49.32; 39.21; 33.81; 29.48; 29.22; 28.52; 26.06; 25.53; and 24.83 ppm; and

MS: 1405.5 (M+).

The above synthetic procedure can be executed with n taking any value from 3 to 15,000 provided that a suitable oligo- or poly-ethylene glycol derivative is used instead of 2-[2-(2-{2-{2-[2-(undec-10-enyloxy)ethoxy]ethoxy}ethoxy)ethoxy]ethoxy}ethanol. If necessary, type and/or amount of solvent and/or reaction time may be adapted in view of n, especially accounting for the physical state (liquid or solid) and the solubility of the polyethyleneglycol involved.

EXAMPLE 9

Synthesis of 2-(2-(2-(2-(11-2-(allyloxy)ethoxy)ethoxy)ethoxy)ethoxy undec-6-ene-1-thinly and Analogues Derived from Higher Polyethylene Glycols 2-(2-(2-(2-(11-2-(allyloxy)ethoxy)ethoxy)ethoxy)ethoxy undec-6-ene-1-thinly is an example of a compound (shown schematically below) of the general formula $X_1$—$(CH_2)_c$—O—$([CH_2]_t$—$CH_2$—$O)_n$—$R_1$—S—$X_2$ wherein $X_1$=alkenyl, c=1, t=1 and $X_2$=H.

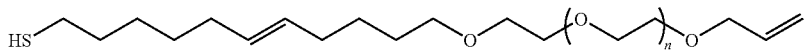

This molecule and is synthesized according to the following scheme:

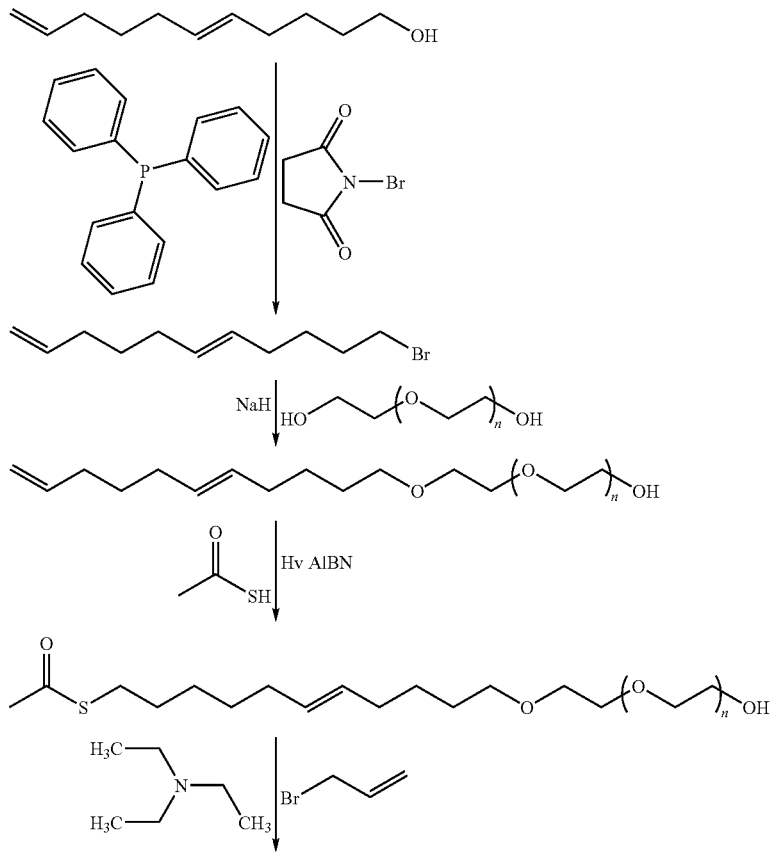

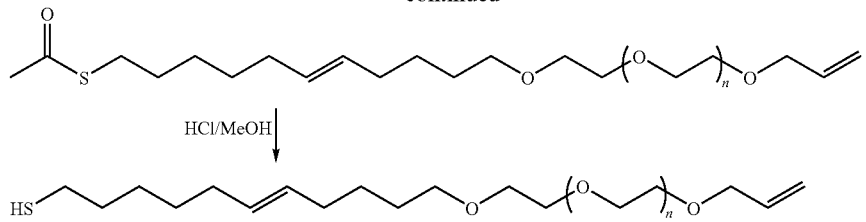

In a first step, in a dry bottle comprising a magnetic stirrer, a ball cooler and under argon atmosphere, 1 molar equivalent of 5,10-undecadien-1-ol (product # S303453-1 EA SigmaAldrich) is dissolved in dry dichloromethane.

The bottle is cooled in a mixture of acetone and dry $CO_2$ (−23° C.). 1 molar equivalent of triphenylphosphine and 1 molar equivalent of N-bromosuccinimide are added. The reaction mixture is stirred for 1 h at a temperature of −23° C. and afterwards for ½ h at room temperature. The solution is extracted with a solution of sodium carbonate. The organic phase is dried on $MgSO_4$. The product is then concentrated using rotary evaporation. Next, the product is extracted with hexane under reflux. The product is filtered via vacuum filtration on alumina (5 cm in height and 3 cm diameter) and washed with hexane. The product is again concentrated using rotary evaporation.

In a second step, in a dry bottle comprising a magnetic stirrer and under argon atmosphere, 2 molar equivalents of triethylene glycol are dissolved in a mixture of THF/DMF. 1 molar equivalent of NaH is added and the solution is stirred for 1 h under an atmosphere of argon. 1 molar equivalent of the product obtained in step 1 is added, and the reaction mixture is stirred for 3 days under an atmosphere of argon.

The product is quenched with MeOH. THF and DMF are removed by rotary evaporation at reduced pressure. The product is extracted with dichloromethane and $H_2O$. The organic phase is dried on $MgSO_4$. The product is then concentrated using rotary evaporation. Next, the product is purified on a silica column using a suitable mixture of organic solvents, known by persons skilled in the art.

The product is again concentrated using rotary evaporation.

In a third step, in a dry bottle comprising a magnetic stirrer and under argon atmosphere, 1 molar equivalent of the product obtained in step 2 is dissolved in Ethanol. 4 molar equivalents of thioacetic acid and 10 mg of 2,2'-azobis(isobutyronitrile) (AIBN) are added and the solution is irradiated for 24 h under an atmosphere of argon. The product is purified by filtering on a glass filter followed by rotary evaporation at reduced pressure and by purification on a silica column using ethylacetate/methanol (95/5).

In a fourth step, in a dry bottle comprising a magnetic stirrer and under argon atmosphere, 1 molar equivalent of the product obtained in step 3, is dissolved in $CH_2Cl_2$. 1.5 molar equivalents of triethylamine is added and the solution is stirred for 1 h under an atmosphere of argon. 1.5 molar equivalents of allyl bromide are then added and the solution is stirred for 24 h under an atmosphere of argon. The product is purified by rotary evaporation at reduced pressure and by purification on a silica column using a suitable mixture of organic solvents, known by persons skilled in the art.

In a fifth step, in a dry bottle comprising a magnetic stirrer and under argon atmosphere, 1 molar equivalent of the product obtained in step 4 is dissolved in a solution containing 1M HCl and MeOH (1/1). The solution is stirred for 24 h. The solution is then extracted with an organic solvent and $H_2O$. The organic phase is dried on $MgSO_4$. The product is then concentrated using rotary evaporation. Next, the product is purified on a silica column using a suitable mixture of organic solvents, known by persons skilled in the art. The product is again concentrated using rotary evaporation.

The above synthetic procedure can be executed with n taking any value from 3 to 15,000 provided that a suitable oligo- or poly-ethylene glycol is used instead of triethylene glycol. If necessary, type and/or amount of solvent and/or reaction time may be adapted in view of n, especially accounting for the physical state (liquid or solid) and the solubility of the polyethyleneglycol involved.

EXAMPLE 10

Synthesis of 2-(2-(2-(allyloxy)ethoxy)ethoxy)ethyl 16-mercapto-6-oxohexadecanoate and Analogues Derived from Higher Polyethylene Glycols 2-(2-(2-(allyloxy)ethoxy)ethoxy)ethyl 16-mercapto-6-oxohexadecanoate is an example of a compound (shown schematically below) of the general formula $X_1$—$(CH_2)_n$—O—$([CH_2]_t$—$CH_2$—$O)_n$—$R_1$—S—$X_2$ wherein $X_1$=alkenyl, c=1, t=1, $X_2$=H and n=3.

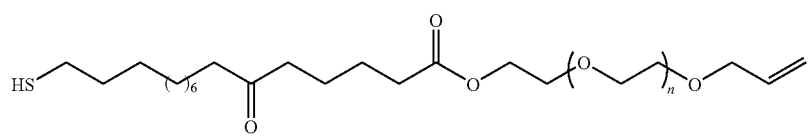

The present molecule is synthesized according to the following synthesis scheme:

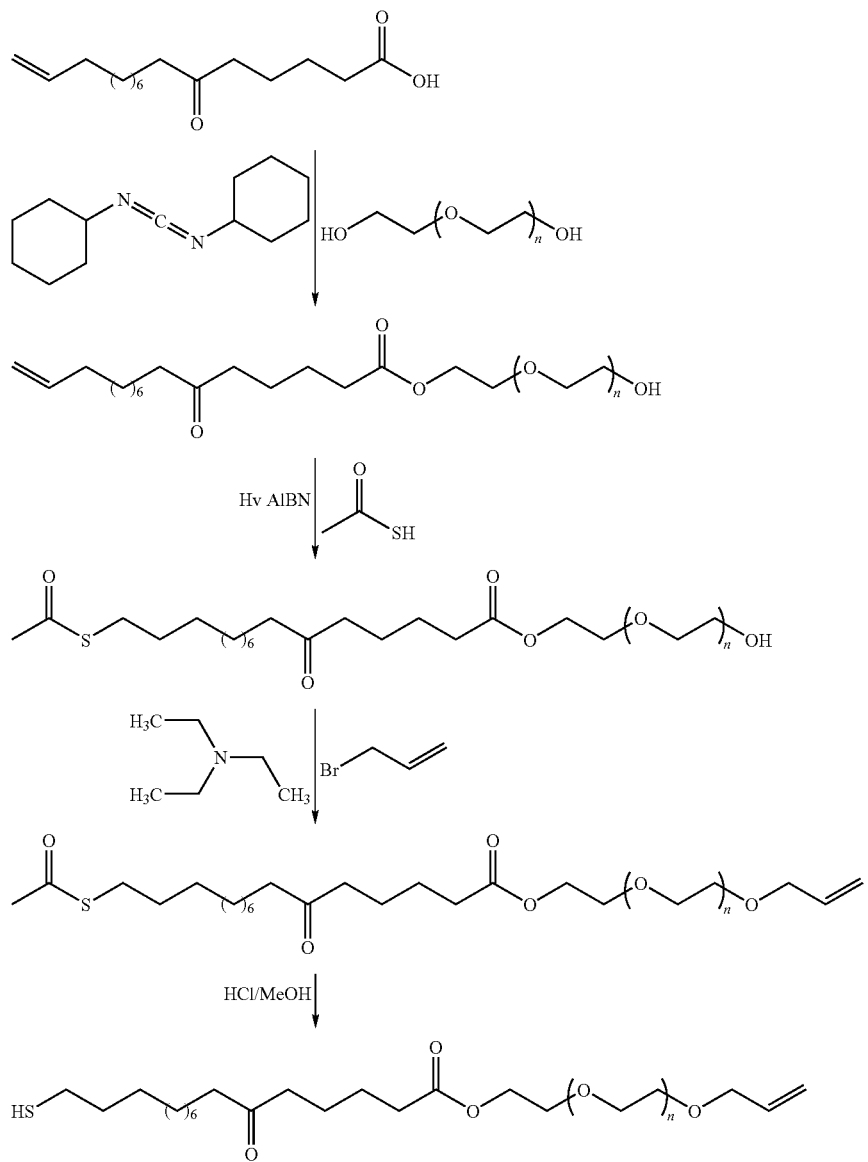

In a first step, in a dry bottle comprising a magnetic stirrer and under argon atmosphere, 1 molar equivalent of 6-oxo-15-hexadecenoic acid and 2 molar equivalents of triethylene glycol are dissolved in dry ethylacetate. The solution is stirred and cooled down to 0° C. 1.2 molar equivalents dicyclohexyl-carbodiimide (DCC) is added and the solution is stirred for 30 min. Next, the solution is stirred for 3 days at room temperature. The product is purified on a silica column using a suitable mixture of organic solvents, known by the person skilled in the art. The resulting product is concentrated using rotary evaporation In a second step, in a dry bottle comprising a magnetic stirrer and under argon atmosphere, 1 molar equivalent of the product obtained in step 1 is dissolved in Ethanol. 4 molar equivalents of thioacetic acid and 10 mg of 2,2'-azobis(isobutyronitrile) (AIBN) are added and the solution is irradiated for 24 h under an atmosphere of argon. The product is purified by filtering on a glass filter followed by rotary evaporation at reduced pressure and by purification on a silica column using ethylacetate/methanol (95/5).

In a third step, in a dry bottle comprising a magnetic stirrer and under argon atmosphere, 1 molar equivalent of the product obtained in step 2, is dissolved in $CH_2Cl_2$. 1.5 molar equivalents of triethylamine is added and the solution is stirred for 1 h under an atmosphere of argon. 1.5 molar equivalents of allyl bromide are then added and the solution is stirred for 24 h under an atmosphere of argon. The product is purified by rotary evaporation at reduced pressure and by purification on a silica column using a suitable mixture of organic solvents, known by the person skilled in the art.

In a fourth step, in a dry bottle comprising a magnetic stirrer and under argon atmosphere, 1 molar equivalent of the product obtained in step 3 is dissolved in a solution containing 1M HCl and MeOH (1/1). The solution is stirred for 24 h. The solution is then extracted with an organic solvent and H$_2$O. The organic phase is dried on MgSO$_4$. The product is then concentrated using rotary evaporation. Next, the product is purified on a silica column using a suitable mixture of organic solvents, known by persons skilled in the art. The product is again concentrated using rotary evaporation.

The above synthetic procedure can be executed with n taking any value from 3 to 15,000 provided that a suitable oligo- or poly-ethylene glycol is used instead of triethylene glycol. If necessary, type and/or amount of solvent and/or reaction time may be adapted in view of n, especially accounting for the physical state (liquid or solid) and the solubility of the polyethyleneglycol involved.

EXAMPLE 11

Synthesis of 2-(2-{2-[2-(11-mercaptoyldisulfanyl-undecyloxy)ethoxy]ethoxy}ethoxy)methyl 2,4-dinitrophenoxycarbonyl 2-(2-{2-[2-(11-mercaptoyldisulfanyl-undecyloxy)ethoxy]ethoxy}ethoxy)methyl 2,4-dinitrophenoxycarbonyl is an example of a compound (shown schematically below) of the general formula X$_1$—(CH$_2$)$_c$—O—([CH$_2$]$_t$—CH$_2$—O)$_n$—R$_1$—S—X$_2$ wherein X$_1$=2,4-dinitrophenoxycarbonyl, c=1 and n=3, t=1, X$_2$=X$_1$—(CH$_2$)$_c$—O—([CH$_2$]$_t$—CH$_2$—O)$_n$—R$_1$—S, and R$_1$=(CH$_2$)$_{11}$.

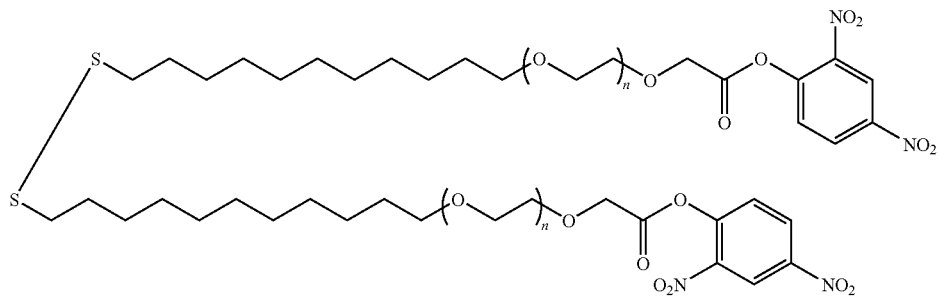

The present molecule is synthesized according to the following synthesis scheme:

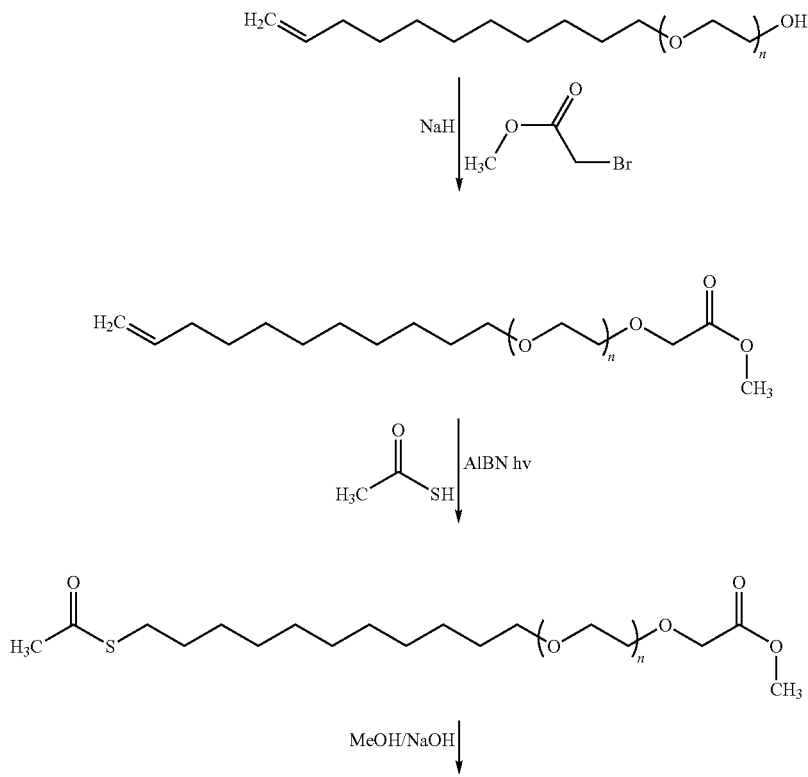

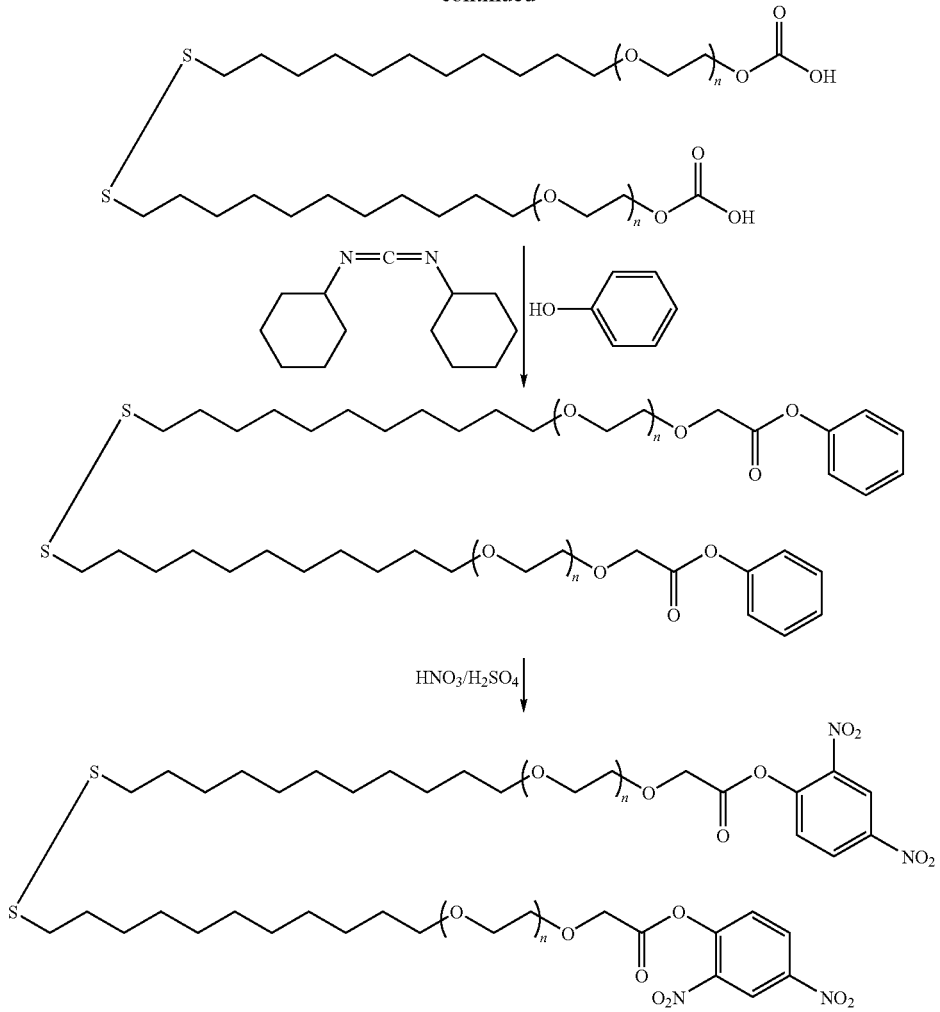

In a first step, in a dry bottle comprising a magnetic stirrer and under argon atmosphere, 1 molar equivalent of 2-{2-[2-(undec-10-enyloxy)ethoxy]ethoxy}ethanol and 1.5 molar equivalents of NaH are dissolved in 50 mL DMF. The solution is stirred for 30 min. 1.5 molar equivalents of methyl bromoacetate is added and the solution is stirred for 24 h under an atmosphere of argon. The product is quenched with 25 mL of methanol. The solution is then extracted with diethyl ether and $H_2O$. The organic phase is dried on $MgSO_4$. The product is then concentrated using rotary evaporation. Next, the product is purified on a silica column using a suitable mixture of organic solvents, known to the person skilled in the art. The resulting product is concentrated using rotary evaporation.

In a second step, in a dry bottle comprising a magnetic stirrer and under argon atmosphere, 1 molar equivalent of the product obtained in step 1 is dissolved in methanol. 4 molar equivalents of thioacetic acid and 10 mg of 2,2'-azobis(isobutyronitrile) (AIBN) are added and the solution is irradiated under UV light for 24 h under an atmosphere of argon. The product is purified by filtering on a glass filter followed by rotary evaporation at reduced pressure and by purification on a silica column using a suitable mixture of organic solvents, known to the person skilled in the art.

In a third step, in a dry bottle comprising a magnetic stirrer and 1 molar equivalent of the product obtained in step 2 is dissolved in a solution containing methanol/1M NaOH (3/1). The solution is stirred for 24 h. HCl is added to acidify the solution. The solution is then extracted with $CH_2Cl_2$ and $H_2O$. The organic phase is dried on $MgSO_4$. The product is purified on a silica column using a suitable mixture of organic solvents, known to the person skilled in the art. The resulting product is concentrated using rotary evaporation.

In a fourth step, in a dry bottle comprising a magnetic stirrer and under argon atmosphere, 1 molar equivalent of the product obtained in step 3 and 1.2 molar equivalent phenol is dissolved in dry ethylacetate. The solution is stirred and cooled down to 0° C. 1.2 molar equivalents dicyclohexylcarbodiimide (DCC) is added and the solution is stirred for 30 min. Next, the solution is stirred for 3 days at room temperature. The product is purified on a silica column using a suitable mixture of organic solvents, known to the person skilled in the art. The resulting product is concentrated using rotary evaporation.

In a fifth step, in a dry bottle comprising a magnetic stirrer and under argon atmosphere, 1 molar equivalent of the product obtained in step 4 and 2 molar equivalents $HNO_3$ in $H_2SO_4$ is added. The solution is stirred for 24 h. The solution is then extracted with organic solvents and H$_2$O. The organic phase is dried on MgSO$_4$. The product is purified on a silica column using a suitable mixture of organic solvents, known to the person skilled in the art. The resulting product is concentrated using rotary evaporation.

The above synthetic procedure can be executed with n taking any value from 3 to 15,000 provided that a suitable oligo- or poly-ethyleneglycol derivative is used instead of 2-{2-[2-(undec-10-enyloxy)ethoxy]ethoxy}ethanol. If necessary, type and/or amount of solvent and/or reaction time may be adapted in view of n, especially accounting for the physical state (liquid or solid) and the solubility of the polyethyleneglycol involved.

EXAMPLE 12

Synthesis of 2-{2-[2-(11-mercapto-undecyloxy)-ethoxy]-ethoxy}-ethoxy propene and Analogues Derived from Higher Polyethylene Glycols 2-{2-[2-(11-mercapto-undecyloxy)-ethoxy]-ethoxy}-ethoxy propene is an example of a compound (shown schematically below) of the general formula X$_1$—(CH$_2$)$_c$—O—([CH$_2$]$_t$—CH$_2$—O)$_n$—R$_1$—S—X$_2$ wherein X$_1$=alkenyl, c=1, t=1, X$_2$=H, and R$_1$=(CH$_2$)$_{11}$, and n=3.

The present molecule is synthesized according to the following synthesis scheme:

In a first step, in a dry bottle comprising a magnetic stirrer and under argon atmosphere, 1 molar equivalent of 2-{2-[2-(undec-10-enyloxy)ethoxy]ethoxy}ethanol is dissolved in Ethanol. 4 molar equivalents of thioacetic acid and 10 mg of 2,2'-azobis(isobutyronitrile) (AIBN) are added and the solution is irradiated for 24 h under an atmosphere of argon. The product is purified by filtering on a glass filter followed by rotary evaporation at reduced pressure and by purification on a silica column using ethylacetate/methanol (95/5).

In a second step, in a dry bottle comprising a magnetic stirrer and under argon atmosphere, 1 molar equivalent of the product obtained in step 1, is dissolved in CH$_2$Cl$_2$. 1.5 molar equivalents of triethylamine is added and the solution is stirred for 1 h under an atmosphere of argon. 1.5 molar equivalents of allyl bromide are then added and the solution is stirred for 24 h under an atmosphere of argon. The product is purified by rotary evaporation at reduced pressure and by purification on a silica column using a suitable mixture of organic solvents, known to the person skilled in the art.

In a third step, in a dry bottle comprising a magnetic stirrer and under argon atmosphere, 1 molar equivalent of the product obtained in step 2 is dissolved in a solution containing 1M HCl and MeOH (1/1). The solution is stirred for 24 h. The solution is then extracted with an organic solvent and H$_2$O. The organic phase is dried on MgSO$_4$. The product is then concentrated using rotary evaporation. Next, the product is purified on a silica column using a suitable mixture of organic solvents, known to the person skilled in the art. The product is again concentrated using rotary evaporation.

The above synthetic procedure can be executed with n taking any value from 3 to 15,000 provided that a suitable oligo- or poly-ethyleneglycol derivative is used instead of 2-{2-[2-(undec-10-enyloxy)ethoxy]ethoxy}ethanol. If nec

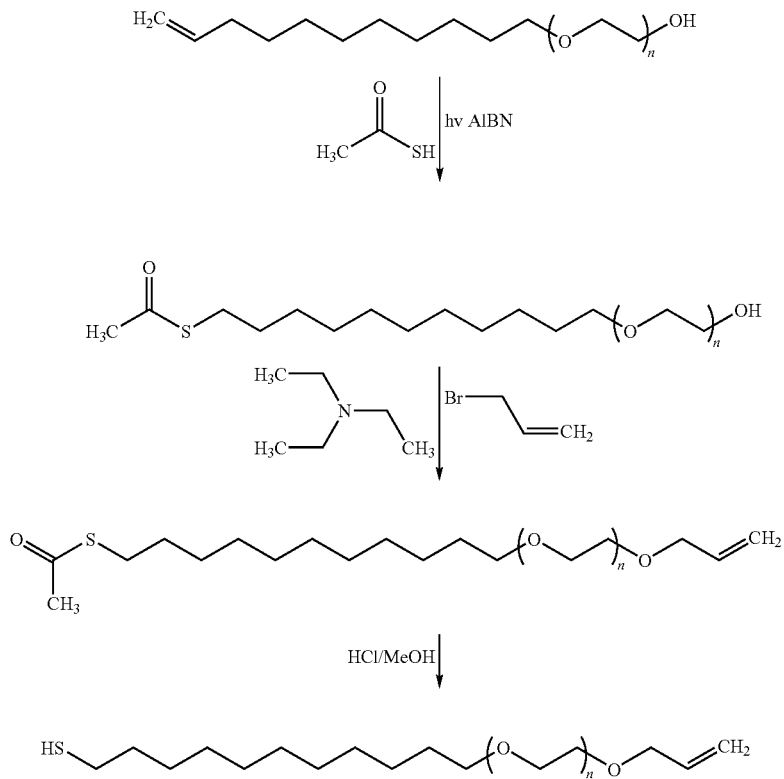

essary, type and/or amount of solvent and/or reaction time may be adapted in view of n, especially accounting for the physical state (liquid or solid) and the solubility of the polyethyleneglycol involved.

EXAMPLE 13

Synthesis of Synthesis of 2-(2-(2-(11-mercapto-undecyloxy)-ethoxy)ethoxy)ethoxy sulfonylchloride and Analogues Derived from Higher Polyethylene Glycols 2-(2-(2-(11-mercapto-undecyloxy)ethoxy)ethoxy)ethoxy sulfonyl chloride is an example of a compound (shown schematically below) of the general formula $X_1—(CH_2)_c—O—([CH_2]_t—CH_2—O)_n—R_1—S—X_2$ wherein $X_1$=sulfonyl chloride, c=0 and n=3, t=1, $X_2$=H, and $R_1$=$(CH_2)_{11}$.

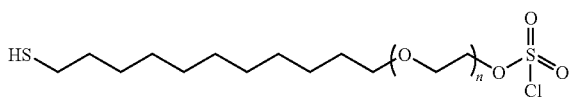

The present molecule is synthesized according to the following synthesis scheme:

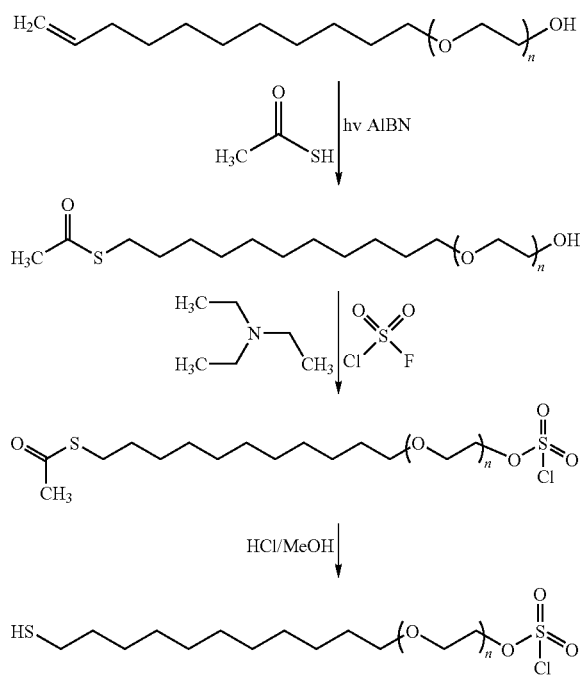

In a first step, in a dry bottle comprising a magnetic stirrer and under argon atmosphere, 1 molar equivalent of 2-{2-[2-(undec-10-enyloxy)ethoxy]ethoxy}ethanol is dissolved in ethanol. 4 molar equivalents of thioacetic acid and 10 mg of 2,2'-azobis(isobutyronitrile) (AIBN) are added and the solution is irradiated for 24 h under an atmosphere of argon. The product is purified by filtering on a glass filter followed by rotary evaporation at reduced pressure and by purification on a silica column using ethylacetate/methanol (95/5).

In a second step, in a dry bottle comprising a magnetic stirrer and under argon atmosphere, 1 molar equivalent of the product obtained in step 1, is dissolved in an organic solvent. 1.5 molar equivalents of triethylamine are added and the solution is stirred for 1 h under an atmosphere of argon. 1.5 molar equivalents of sulfuryl chloride fluoride are then added and the solution is stirred for 24 h under an atmosphere of argon. The product is purified by rotary evaporation at reduced pressure and by purification on a silica column using a suitable mixture of organic solvents, known by the person skilled in the art.

In a third step, in a dry bottle comprising a magnetic stirrer and under argon atmosphere, 1 molar equivalent of the product obtained in step 2 is dissolved in a solution containing 1M HCl and MeOH (1/1). The solution is stirred for 24 h. The solution is then extracted with an organic solvent and $H_2O$. The organic phase is dried on $MgSO_4$. The product is then concentrated using rotary evaporation. Next, the product is purified on a silica column using a suitable mixture of organic solvents, known to the person skilled in the art. The product is again concentrated using rotary evaporation.

The above synthetic procedure can be executed with n taking any value from 3 to 15,000 provided that a suitable oligo- or poly-ethyleneglycol derivative is used instead of 2-{2-[2-(undec-10-enyloxy)ethoxy]ethoxy}ethanol. If necessary, type and/or amount of solvent and/or reaction time may be adapted in view of n, especially accounting for the physical state (liquid or solid) and the solubility of the polyethyleneglycol involved.

EXAMPLE 14

Synthesis of 2-(2-(2-(11-mercaptoyldisulfanyl-undecyloxy)-ethoxy)ethoxy)ethoxy sulfonylchloride and Analogues Derived from Higher Polyethylene Glycols

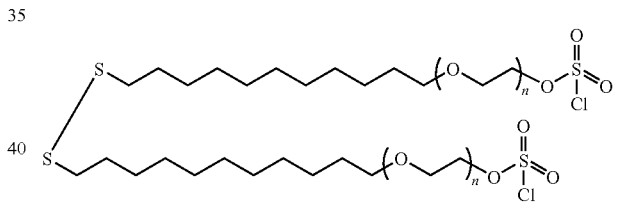

2-(2-(2-(11-mercaptoyldisulfanyl-undecyloxy)-ethoxy)ethoxy)ethoxy sulfonylchloride is an example of a compound (shown schematically below) of the general formula $X_1—(CH_2)_c—O—([CH_2]_t—CH_2—O)_n—R_1—S—X_2$ wherein $X_1$=sulfonyl chloride, c=0 and n=3, t=1, $X_2$=$X_1—(CH_2)_c—O—([CH_2]_t—CH_2—O)_n—R_1—S$, and $R_1$=$(CH_2)_{11}$.

This molecule is synthesized according to the following scheme:

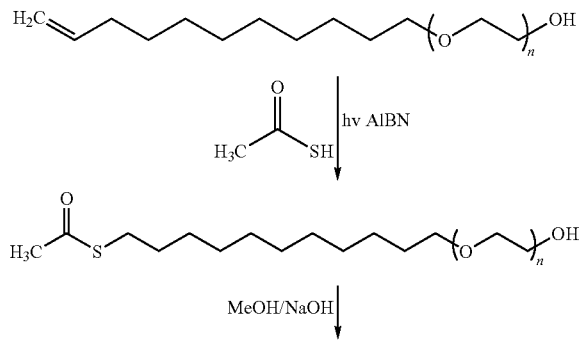

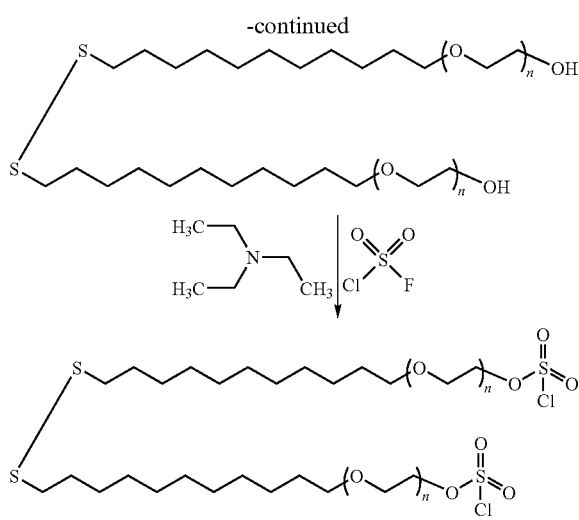

In a first step, in a dry bottle comprising a magnetic stirrer and under argon atmosphere, 1 molar equivalent of 2-{2-[2-(undec-10-enyloxy)ethoxy]ethoxy}ethanol is dissolved in Ethanol. 4 molar equivalents of thioacetic acid and 10 mg of 2,2'-azobis(isobutyronitrile) (AIBN) are added and the solution is irradiated under UV for 24 h under an atmosphere of argon. The product is purified by filtering on a glass filter followed by rotary evaporation at reduced pressure and by purification on a silica column using ethylacetate/methanol (95/5).

In a second step, in a dry bottle comprising a magnetic stirrer and 1 molar equivalent of the product obtained in step 1 is dissolved in a solution containing methanol/1M NaOH (3/1). The solution is stirred for 24 h. The solution is then extracted with an organic solvent and $H_2O$. The organic phase is dried on $MgSO_4$. The product is purified on a silica column using a suitable mixture of organic solvents, known the person skilled in the art. The resulting product is concentrated using rotary evaporation.

In a third step, in a dry bottle comprising a magnetic stirrer and under argon atmosphere, 1 molar equivalent of the product obtained in step 2, is dissolved in an organic solvent. 1.5 molar equivalents of triethylamine are added and the solution is stirred for 1 h under an atmosphere of argon. 1.5 molar equivalents of sulfuryl chloride fluoride are then added and the solution is stirred for 24 h under an atmosphere of argon. The product is purified by rotary evaporation at reduced pressure and by purification on a silica column using a suitable mixture of organic solvents, known to the person skilled in the art.

The above synthetic procedure can be executed with n taking any value from 3 to 15,000 provided that a suitable oligo- or poly-ethyleneglycol derivative is used instead of 2-{2-[2-(undec-10-enyloxy)ethoxy]ethoxy}ethanol. If necessary, type and/or amount of solvent and/or reaction time may be adapted in view of n, especially accounting for the physical state (liquid or solid) and the solubility of the polyethyleneglycol involved.

EXAMPLE 15

Synthesis of 2-(2-(2-(2-(11-mercaptoyldisulfanyl-undecyloxy)-ethoxy)ethoxy)ethoxy)methyl isothiocyanate and Analogues Derived from Higher Polyethylene Glycols 2-(2-(2-(2-(11-mercaptoyldisulfanyl-undecyloxy)-ethoxy)ethoxy)ethoxy)methyl isothiocyanate is an example of a compound (shown schematically below) of the general formula $X_1$—$(CH_2)_c$—O—$([CH_2]_t$—$CH_2$—O$)_n$—$R_1$—S—$X_2$ wherein $X_1$=isothiocyanato, c=1 and n=3, t=1, $X_2$=$X_1$—$(CH_2)_c$—O—$([CH_2]_t$—$CH_2$—O$)_n$—$R_1$—S, and $R_1$=$(CH_2)_{11}$.

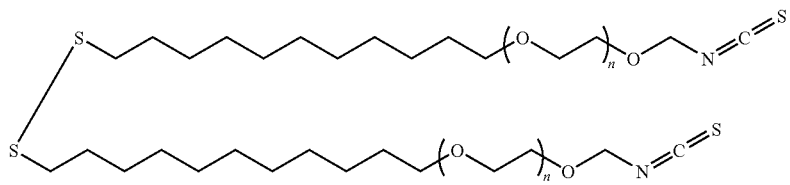

The present molecule is synthesized according to the following synthesis scheme:

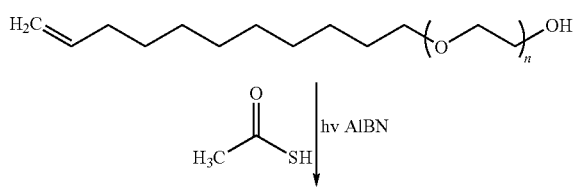

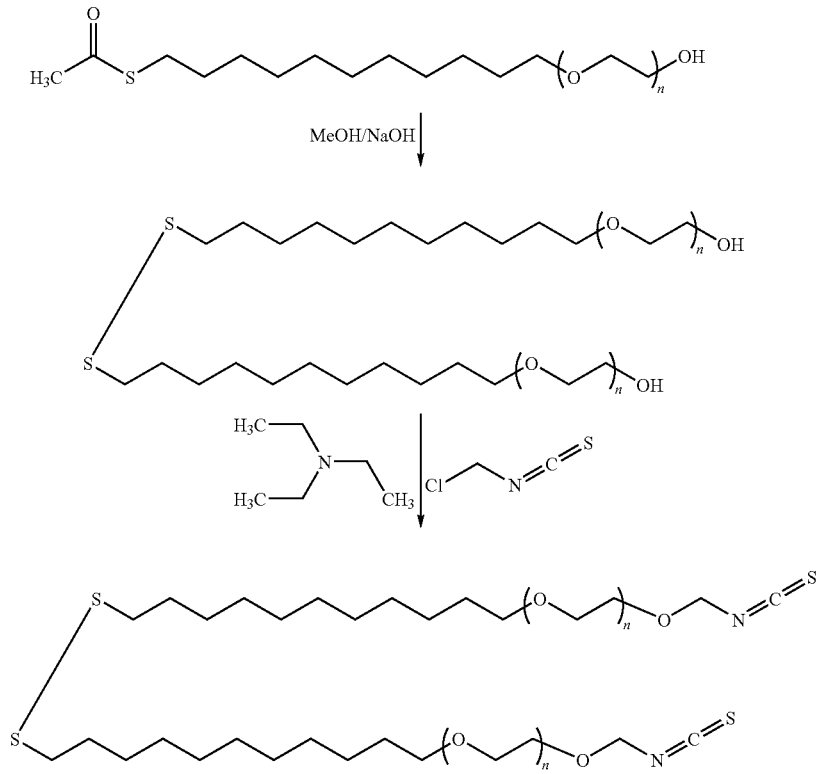

In a first step, in a dry bottle comprising a magnetic stirrer and under argon atmosphere, 1 molar equivalent of 2-{2-[2-(undec-10-enyloxy)ethoxy]ethoxy}ethanol is dissolved in Ethanol. 4 molar equivalents of thioacetic acid and 10 mg of 2,2'-azobis(isobutyronitrile) (AIBN) are added and the solution is irradiated for 24 h under an atmosphere of argon. The product is purified by filtering on a glass filter followed by rotary evaporation at reduced pressure and by purification on a silica column using ethylacetate/methanol (95/5).

In a second step, in a dry bottle comprising a magnetic stirrer and 1 molar equivalent of the product obtained in step 1 is dissolved in a solution containing methanol/1M NaOH (3/1). The solution is stirred for 24 h. The solution is then extracted with an organic solvent and $H_2O$. The organic phase is dried on $MgSO_4$. The product is purified on a silica column using a suitable mixture of organic solvents, known to the person skilled in the art. The resulting product is concentrated using rotary evaporation.

In a third step, in a dry bottle comprising a magnetic stirrer and under argon atmosphere, 1 molar equivalent of the product obtained in step 2, is dissolved in an organic solvent. 1.5 molar equivalents of triethylamine are added and the solution is stirred for 1 h under an atmosphere of argon. 1.5 molar equivalents of chloromethyl thiocyanate are then added and the solution is stirred for 24 h under an atmosphere of argon. The product is purified by rotary evaporation at reduced pressure and by purification on a silica column using a suitable mixture of organic solvents, known to the person skilled in the art.

The above synthetic procedure can be executed with n taking any value from 3 to 15,000 provided that a suitable oligo- or poly-ethyleneglycol derivative is used instead of 2-{2-[2-(undec-10-enyloxy)ethoxy]ethoxy}ethanol. If necessary, type and/or amount of solvent and/or reaction time may be adapted in view of n, especially accounting for the physical state (liquid or solid) and the solubility of the polyethyleneglycol involved.

EXAMPLE 16

Synthesis of 2-(2-(2-(2-(11-mercapto-undecyloxy)-ethoxy)ethoxy)ethoxy)methyl isothiocyanate and Analogues Derived from Higher Polyethylene Glycols 2-(2-(2-(2-(11-mercapto-undecyloxy)ethoxy)ethoxy)ethoxy)methyl isothiocyanate is an example of a compound (shown schematically below) of the general formula $X_1$—$(CH_2)_c$—O—$([CH_2]_t$—$CH_2$—$O)_n$—$R_1$—S—$X_2$ wherein $X_1$=isothiocyanato, c=1, t=1, $X_2$=H, and $R_1$=$(CH_2)_{11}$, and n=3.

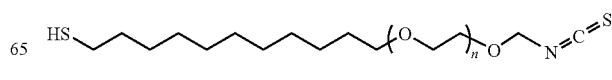

The present molecule is synthesized according to the following synthesis scheme:

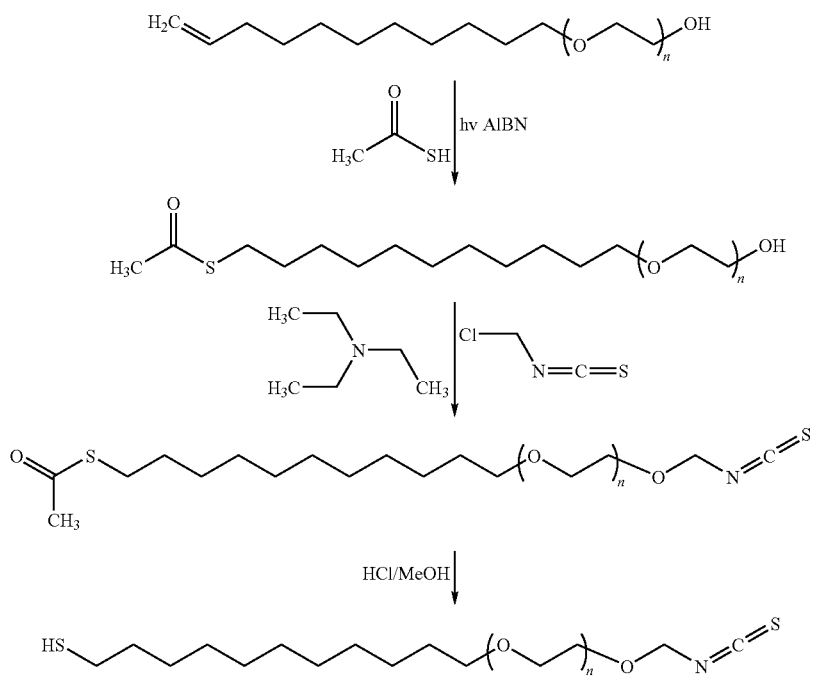

In a first step, in a dry bottle comprising a magnetic stirrer and under argon atmosphere, 1 molar equivalent of 2-{2-[2-(undec-10-enyloxy)ethoxy]ethoxy}ethanol is dissolved in Ethanol. 4 molar equivalents of thioacetic acid and 10 mg of 2,2'-azobis(isobutyronitrile) (AIBN) are added and the solution is irradiated for 24 h under an atmosphere of argon. The product is purified by filtering on a glass filter followed by rotary evaporation at reduced pressure and by purification on a silica column using ethylacetate/methanol (95/5).

In a second step, in a dry bottle comprising a magnetic stirrer and under argon atmosphere, 1 molar equivalent of the product obtained in step 1, is dissolved in $CH_2Cl_2$. 1.5 molar equivalents of triethylamine is added and the solution is stirred for 1 h under an atmosphere of argon. 1.5 molar equivalents of chloromethyl thiocyanate are then added and the solution is stirred for 24 h under an atmosphere of argon. The product is purified by rotary evaporation at reduced pressure and by purification on a silica column using a suitable mixture of organic solvents, known to the person skilled in the art.

In a third step, in a dry bottle comprising a magnetic stirrer and under argon atmosphere, 1 molar equivalent of the product obtained in step 2 is dissolved in a solution containing 1M HCl and MeOH (1/1). The solution is stirred for 24 h. The solution is then extracted with an organic solvent and $H_2O$. The organic phase is dried on $MgSO_4$. The product is then concentrated using rotary evaporation Next, the product is purified on a silica column using a suitable mixture of organic solvents, known to the person skilled in the art. The product is again concentrated using rotary evaporation.

The above synthetic procedure can be executed with n taking any value from 3 to 15,000 provided that a suitable oligo- or poly-ethyleneglycol derivative is used instead of 2-{2-[2-(undec-10-enyloxy)ethoxy]ethoxy}ethanol. If necessary, type and/or amount of solvent and/or reaction time may be adapted in view of n, especially accounting for the physical state (liquid or solid) and the solubility of the polyethyleneglycol involved.

EXAMPLE 17

Synthesis of 2-(2-(2-(2-(11-mercaptoundecyloxy)ethoxy)ethoxy)methyl 1,3-chloropropanone and Analogues Derived from Higher Polyethylene Glycols 2-(2-(2-(2-(11-mercaptoundecyloxy)ethoxy)ethoxy)ethoxy)methyl 1,3-chloropropanone is an example of a compound (shown schematically below) of the general formula $X_1$—$(CH_2)_c$—O—$([CH_2]_t$—$CH_2$—O$)_n$—$R_1$—S—$X_2$ wherein $X_1$=chloroalkylcarbonyl, c=1, t=1, $X_2$=H, and $R_1$=$(CH_2)_{11}$, and n=3.

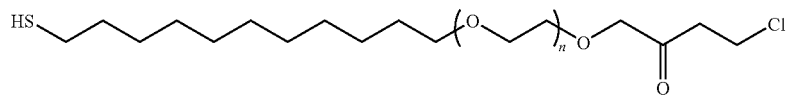

The present molecule is synthesized according to the following synthesis scheme:

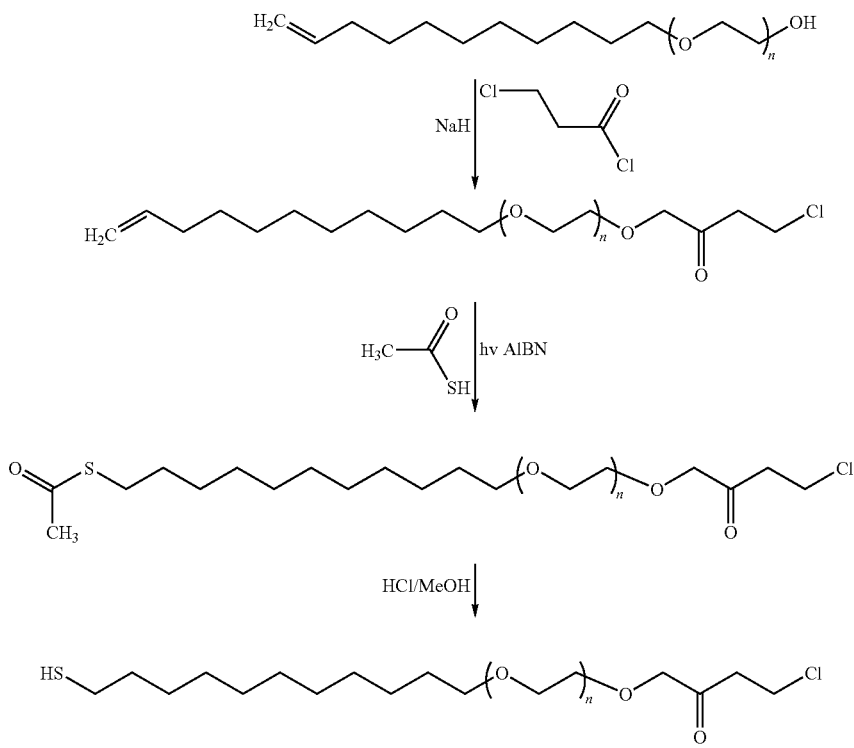

In a first step, in a dry bottle comprising a magnetic stirrer and under argon atmosphere, 1 molar equivalent of 2-{2-[2-(undec-10-enyloxy)ethoxy]ethoxy}ethanol and 1.5 molar equivalents of NaH are dissolved in 50 mL DMF. The solution is stirred for 30 min. 1.5 molar equivalents of 3-chloropropionyl chloride is added and the solution is stirred for 24 h under an atmosphere of argon. The product is quenched with 25 mL of methanol. The solution is then extracted with an organic solvent and $H_2O$. The organic phase is dried on $MgSO_4$. The product is then concentrated using rotary evaporation. Next, the product is purified on a silica column using a suitable mixture of organic solvents, known to the person skilled in the art. The resulting product is concentrated using rotary evaporation.

In a second step, in a dry bottle comprising a magnetic stirrer and under argon atmosphere, 1 molar equivalent of the product obtained in step 1 is dissolved in methanol. 4 molar equivalents of thioacetic acid and 10 mg of 2,2'-azobis(isobutyronitrile) (AIBN) are added and the solution is irradiated under UV light for 24 h under an atmosphere of argon. The product is purified by filtering on a glass filter followed by rotary evaporation at reduced pressure and by purification on a silica column using a suitable mixture of organic solvents, known to the person skilled in the art.

In a third step, in a dry bottle comprising a magnetic stirrer and under argon atmosphere, 1 molar equivalent of the product obtained in step 2 is dissolved in a solution containing 1M HCl and EtOH (1/1). The solution is stirred for 24 h. The solution is then extracted with an organic solvent and $H_2O$. The organic phase is dried on $MgSO_4$. The product is then concentrated using rotary evaporation.

Next, the product is purified on a silica column using a suitable mixture of organic solvents, known to the person skilled in the art. The product is again concentrated using rotary evaporation.

The above synthetic procedure can be executed with n taking any value from 3 to 15,000 provided that a suitable oligo- or poly-ethyleneglycol derivative is used instead of 2-{2-[2-(undec-10-enyloxy)ethoxy]ethoxy}ethanol. If necessary, type and/or amount of solvent and/or reaction time may be adapted in view of n, especially accounting for the physical state (liquid or solid) and the solubility of the polyethyleneglycol involved.

EXAMPLE 18

Synthesis of 2-(2-(2-(2-(11-mercaptoundecyloxy)ethoxy)-ethoxy)ethoxy)methyl 4-fluorophenyl and Analogues Derived from Higher Polyethylene Glycols 2-(2-(2-(2-(11-mercaptoundecyloxy)ethoxy)ethoxy)ethoxy)methyl 4-fluorophenyl is an example of a compound (shown schematically below) of the general formula $X_1$—$(CH_2)_c$—O—$([CH_2]_t$—$CH_2$—O$)_n$—$R_1$—S—$X_2$ wherein $X_1$=fluorophenyl, c=1, t=1, $X_2$=H, and $R_1$=$(CH_2)_{11}$, and n=3:

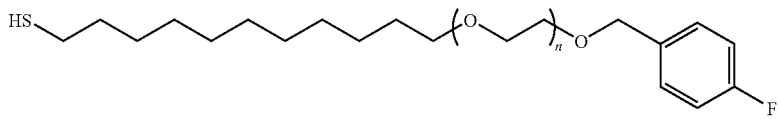

The present molecule is synthesized according to the following synthesis scheme:

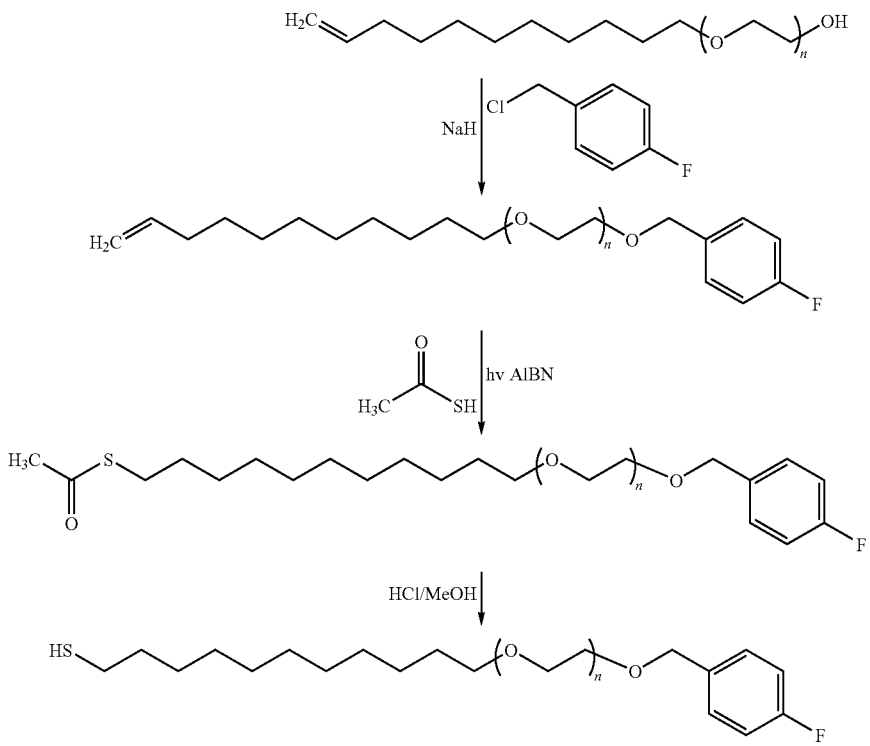

In a first step, in a dry bottle comprising a magnetic stirrer and under argon atmosphere, 1 molar equivalent of 2-{2-[2-(undec-10-enyloxy)ethoxy]ethoxy}ethanol and 1.5 molar equivalents of NaH are dissolved in 50 mL DMF. The solution is stirred for 30 min. 1.5 molar equivalents of 4-fluorobenzylchloride is added and the solution is stirred for 24 h under an atmosphere of argon. The product is quenched with 25 mL of methanol. The solution is then extracted with an organic solvent and $H_2O$. The organic phase is dried on $MgSO_4$. The product is then concentrated using rotary evaporation. Next, the product is purified on a silica column using a suitable mixture of organic solvents, known to the person skilled in the art. The resulting product is concentrated using rotary evaporation.

In a second step, in a dry bottle comprising a magnetic stirrer and under argon atmosphere, 1 molar equivalent of the product obtained in step 1 is dissolved in methanol. 4 molar equivalents of thioacetic acid and 10 mg of 2,2'-azobis(isobutyronitrile) (AIBN) are added and the solution is irradiated for 24 h under an atmosphere of argon. The product is purified by filtering on a glass filter followed by rotary evaporation at reduced pressure and by purification on a silica column using a suitable mixture of organic solvents, known to the person skilled in the art.

In a third step, in a dry bottle comprising a magnetic stirrer and under argon atmosphere, 1 molar equivalent of the product obtained in step 2 is dissolved in a solution containing 1M HCl and EtOH (1/1). The solution is stirred for 24 h. The solution is then extracted with an organic solvent and $H_2O$. The organic phase is dried on $MgSO_4$. The product is then concentrated using rotary evaporation. Next, the product is purified on a silica column using a suitable mixture of organic solvents, known to the person skilled in the art. The product is again concentrated using rotary evaporation.

The above synthetic procedure can be executed with n taking any value from 3 to 15,000 provided that a suitable oligo- or poly-ethyleneglycol derivative is used instead of 2-{2-[2-(undec-10-enyloxy)ethoxy]ethoxy}ethanol. If necessary, type and/or amount of solvent and/or reaction time may be adapted in view of n, especially accounting for the physical state (liquid or solid) and the solubility of the polyethyleneglycol involved.

EXAMPLE 19

Synthesis of 2,4-(2-(2-(2-(2-(11-mercaptoundecyloxy)ethoxy)ethoxy)ethoxy)methyl-difluorophenyl and Analogues Derived from Higher Polyethylene Glycols The same procedure as described for Example 18 is followed but the starting material 4-fluorobenzylchloride is replaced by alpha-bromo-2,4-difluorotoluene.

EXAMPLE 20

Synthesis of Synthesis of 3,4-(2-(2-(2-(2-(11-mercaptoundecyloxy)ethoxy)ethoxy)ethoxy)methyl difluorophenyl and Analogues Derived from Higher Polyethylene Glycols The same procedure as described for Example 18 is followed but the starting material 4-fluorobenzylchloride is replaced by alpha-bromo-3,4-difluorotoluene.

EXAMPLE 21

Synthesis of 2,3,4,5-(2-(2-(2-(2-(11-mercaptoundecyloxy)ethoxy)ethoxy)ethoxy)methyl-tetrafluorophenyl and Analogues Derived from Higher Polyethylene Glycols The same procedure as described for Example 18 is followed but the starting material 4-fluorobenzylchloride is replaced by 2,3,4,5-tetrafluorobenzylbromide

EXAMPLE 22

Synthesis of 2,3,4,5,6-(2-(2-(2-(2-(11-mercaptoundecyloxy)-ethoxy)ethoxy)ethoxy)methyl-pentafluorophenyl and Analogues Derived from Higher Polyethylene Glycols 2,3,4,5,6-(2-(2-(2-(2-(11-mercaptoundecyloxy)ethoxy)ethoxy)ethoxy)methyl pentafluorophenyl is an example of a compound (shown schematically below) of the general formula $X_1$—$(CH_2)_n$—$(O$—$[CH_2]_t$—$CH_2)_n$—$O$—$R_1$—$S$—$X_2$ wherein $X_1$ pentafluorophenyl, c=1, t=1, $X_2$=H, and $R_1$=$(CH_2)_{11}$, and n=3.

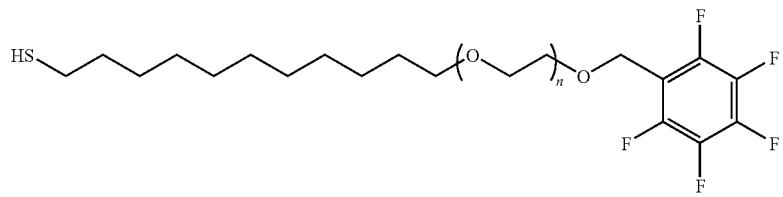

The present molecule can be synthesized according to the following synthesis scheme:

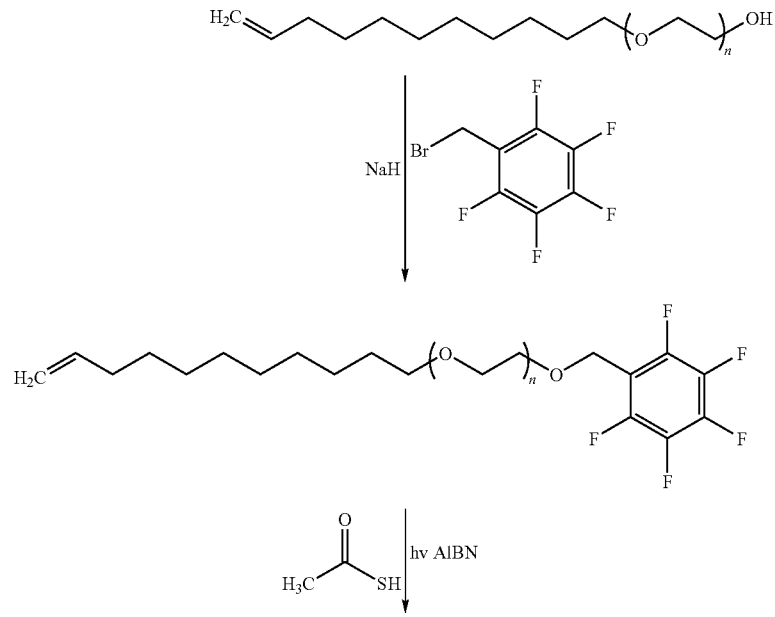

-continued

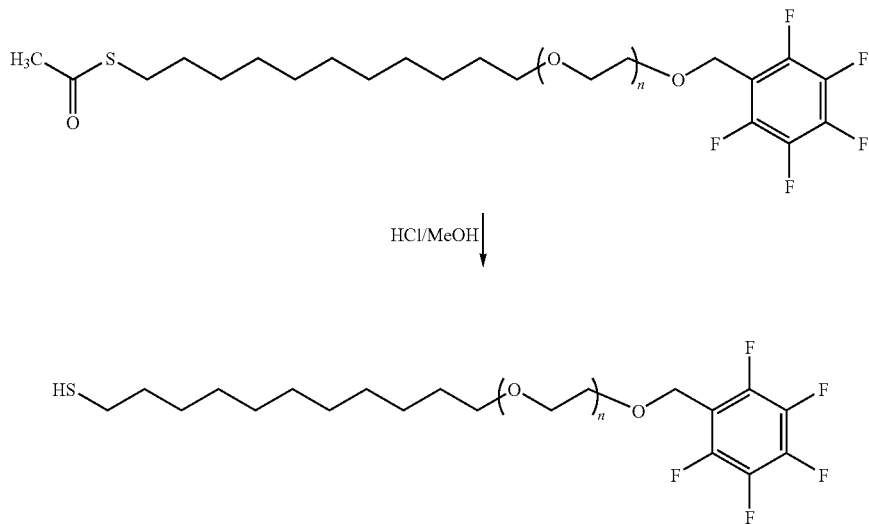

HCl/MeOH

In a first step, in a dry bottle comprising a magnetic stirrer and under argon atmosphere, 1 molar equivalent of 2-{2-[2-(undec-10-enyloxy)ethoxy]ethoxy}ethanol and 1.5 molar equivalents of NaH are dissolved in 50 mL DMF. The solution is stirred for 30 min. 1.5 molar equivalents of alpha-bromo-2,3,4,5,6-pentafluorotoluene is added and the solution is stirred for 24 h under an atmosphere of argon. The product is quenched with 25 mL of methanol. The solution is then extracted with an organic solvent and $H_2O$. The organic phase is dried on $MgSO_4$. The product is then concentrated using rotary evaporation. Next, the product is purified on a silica column using a suitable mixture of organic solvents, known by persons skilled in the art. The resulting product is concentrated using rotary evaporation.

In a second step, in a dry bottle comprising a magnetic stirrer and under argon atmosphere, 1 molar equivalent of the product obtained in step 1 is dissolved in methanol. 4 molar equivalents of thioacetic acid and 10 mg of 2,2'-azobis(isobutyronitrile) (AIBN) are added and the solution is irradiated for 24 h under an atmosphere of argon. The product is purified by filtering on a glass filter followed by rotary evaporation at reduced pressure and by purification on a silica column using a suitable mixture of organic solvents, known to the person skilled in the art.

In a third step, in a dry bottle comprising a magnetic stirrer and under argon atmosphere, 1 molar equivalent of the product obtained in step 2 is dissolved in a solution containing 1M HCl and EtOH (1/1). The solution is stirred for 24 h. The solution is then extracted with an organic solvent and $H_2O$. The organic phase is dried on $MgSO_4$. The product is then concentrated using rotary evaporation. Next, the product is purified on a silica column using a suitable mixture of organic solvents, known to the person skilled in the art. The product is again concentrated using rotary evaporation.

The above synthetic procedure can be executed with n taking any value from 3 to 15,000 provided that a suitable oligo- or poly-ethyleneglycol derivative is used instead of 2-{2-[2-(undec-10-enyloxy)ethoxy]ethoxy}ethanol. If necessary, type and/or amount of solvent and/or reaction time may be adapted in view of n, especially accounting for the physical state (liquid or solid) and the solubility of the polyethyleneglycol involved.

EXAMPLE 23

Synthesis of 2(-2(-2-(11 mercaptoundecyloxy)ethoxy)ethoxy)ethyl-4-fluorobenzoate and Analogues Derived from Higher Polyethylene Glycols The same procedure as described for Example 1 is followed but the starting material pentafluorobenzoyl chloride in the second step is replaced by 4-fluorobenzoylchloride.

EXAMPLE 24

Synthesis of 2(-2(-2-(11 mercaptoundecyloxy)ethoxy)ethoxy)ethyl 3,4-difluorobenzoate and Analogues Derived from Higher Polyethylene Glycols The same procedure as described for Example 1 is followed but the starting material pentafluorobenzoyl chloride in the second step is replaced by 3,4-difluorobenzoylchloride.

EXAMPLE 25

Synthesis of 2(-2(-2-(11 mercaptoundecyloxy)ethoxy)ethoxy)ethyl-2,4-difluorobenzoate and Analogues Derived from Higher Polyethylene Glycols The same procedure as described for Example 1 is followed but the starting material pentafluorobenzoyl chloride in the second step is replaced by 2,4-difluorobenzoylchloride.

EXAMPLE 26

Synthesis of 2(-2(-2-(11 mercaptoundecyloxy) ethoxy)ethoxy)ethyl-3,4,5-trifluorobenzoate and Analogues Derived from Higher Polyethylene Glycols The same procedure as described for Example 1 is followed but the starting material pentafluorobenzoyl chloride in the second step is replaced by 3,4,5-trifluorobenzoylchloride.

EXAMPLE 27

Synthesis of 2(-2(-2-(11-mercaptoundecyloxy) ethoxy)ethoxy)ethyl-2,3,4-trifluorobenzoate and Analogues Derived from Higher Polyethylene Glycols The same procedure as described for Example 1 is followed but the starting material pentafluorobenzoyl chloride in the second step is replaced by 2,3,4-trifluorobenzoylchloride.

EXAMPLE 28

Synthesis of 2(-2(-2-(11 mercaptoundecyloxy) ethoxy)ethoxy)ethyl-2,4,5-trifluorobenzoate and Analogues Derived from Higher Polyethylene Glycols The same procedure as described for Example 1 is followed but the starting material pentafluorobenzoyl chloride in the second step is replaced by 2,4,5-trifluorobenzoylchloride.

EXAMPLE 29

Synthesis of 2(-2(-2-(11 mercaptoundecyloxy) ethoxy)ethoxy)ethyl-2,3,4,5-tetrafluorobenzoate and Analogues Derived from Higher Polyethylene Glycol The same procedure as described for Example 1 is followed but the starting material pentafluorobenzoyl chloride in the second step is replaced by 2,3,4,5 tetrafluorobenzoylchbride.

EXAMPLE 30

Method for Preparing a Device According to the Third Aspect.

In the third aspect, the step of contacting the metal layer with one or more molecules according to the first aspect can for instance be performed in the following way:

The metal substrate such as gold is cleaned using $UV/O_3$ treatment. The molecules can be deposited from a water-free organic solvent like for example tetrahydrofuran (THF). The metal substrates are deposited in this (for example 1 mM) solution and the optimal time (at least 3h) is used to organize the thiols into a self-assembled monolayer (SAM). Afterwards the substrate with the SAM is rinsed with THF and dried with nitrogen. Next step is putting this substrate in a solution with the recognition molecules. The recognition molecules will covalently bind without any activation step.

EXAMPLE 31

Method for Preparing a Device According to the Third Aspect.

The metal substrate such as gold is cleaned using $UV/O_3$ treatment. The molecules can be deposited from a water-free organic solvent like for example tetrahydrofuran (THF). The metal substrates are deposited in this (for example 1 mM) solution containing a mixture of molecules according to the first aspect and molecules of the formula $Y_1$—$([CH_2]_t$—$CH_2$—$O)_n$—$R_3$—$S$—$Y_2$ in chosen proportions. The optimal time (at least 3h) is used to organize the thiols into a self-assembled monolayer (SAM). Afterwards the substrate with the SAM is rinsed with THF and dried with nitrogen. Next step is putting this substrate in a solution with the recognition molecules. The recognition molecules will covalently bind without any activation step.

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this

What is claimed is:

1. A molecule having a structural formula:

X$_1$—(CH$_2$)$_c$—O—([CH$_2$]$_t$—CH$_2$—O)$_n$—R$_1$—S—X$_2$ wherein:

X$_2$ is selected from the group consisting of —H and —S—R$_5$;

R$_5$ is an organic spacer selected from the group consisting of —R$_2$—(O—CH$_2$—[CH$_2$]$_t$)$_n$—O—(CH$_2$)$_c$—X$_1$' and —R$_3$—(O—CH$_2$—[CH$_2$]$_t$)$_n$—Y$_1$;

t is 1 or 2;

c is an integer from 0 to 3;

n is an integer from 3 to 15,000;

R$_1$, R$_2$ and R$_3$ are each independently a saturated or ethylenically unsaturated hydrocarbyl group having from 3 to 30 carbon atoms, wherein the hydrocarbyl group is independently selected from the group consisting of alkyl, alkenyl, cycloalkyl, cycloalkyl-alkyl, cycloalkenyl, cycloalkenylalkyl, and cycloalkylalkenyl, wherein the hydrocarbyl group is independently unsubstituted or substituted with at least one substituent selected from the group consisting of a heteroatom in a main chain and an oxo substituent, wherein the heteroatom is independently selected from the group consisting of nitrogen, oxygen and sulfur;

Y$_1$ is selected from the group consisting of hydroxy and methoxy;

X$_1$ is selected from the group consisting of fluorophenyl, fluorobenzoyl, fluorophenoxycarbonyl, nitrophenoxycarbonyl, sulfonyl halide, isothiocyanato, isocyanato, carbonyl halide, haloalkylcarbonyl, and diazonium carbonyl; and X$_1$' is selected from the group consisting of fluorophenyl, fluorobenzoyl, fluorophenoxycarbonyl, nitrophenoxycarbonyl, oxiranyl, aziridinyl, C$_{2-12}$ alkenyl, iminoether, dichlorotriazinyl, sulfonyl halide, alkoxycarbonyl, isothiocyanato, isocyanato, carbonyl halide, haloalklcarbonyl, carboxlic acid anhydride, diazonium carbonyl N-(2- oxotetrahydro-3-thienyl) amido, and N-carboxy-thiazolidinl-2-thione.

2. The molecule of claim 1, wherein X$_1$ is a fluorophenoxycarbonyl.

3. The molecule of claim 2, wherein X$_1$ is pentafluorophenoxycarbonyl.

4. The molecule of claim 1, wherein X$_2$ is —S—R$_5$.

5. The molecule of claim 1, wherein X$_2$ is —S—R$_2$—(O—CH$_2$—[CH$_2$]$_t$)$_n$—O—(CH$_2$)$_c$—X$_1$'

6. The molecule of claim 1, wherein t is 1.

7. The molecule of claim 1, wherein c is 1.

8. The molecule of claim 1, wherein n is 6.

9. The molecule of claim 1, wherein R$_1$ is a saturated hydrocarbyl group having from 3 to 30 carbon atoms.

10. The molecule of claim 9, wherein the saturated hydrocarbyl group is an alkyl group.

11. The molecule of claim 1, having a formula:

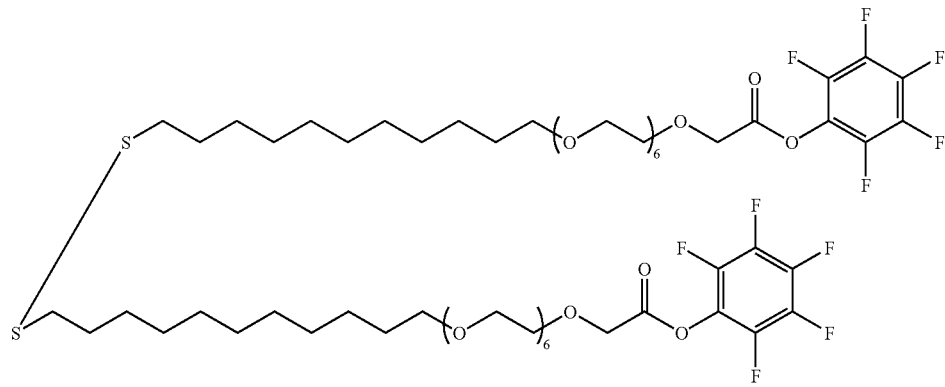

12. The molecule of claim 1, wherein $X_1$ is fluorophenyl.
13. The molecule of claim 1, wherein $X_1$ is fluorobenzoyl.
14. The molecule of claim 1, wherein $X_1$ is nitrophenoxycarbonyl.
15. The molecule of claim 1, wherein $X_1$ is sulfonyl halide.
16. The molecule of claim 1, wherein $X_1$ is isothiocyanato.
17. The molecule of claim 1, wherein $X_1$ is isocyanato.
18. The molecule of claim 1, wherein $X_1$ is carbonyl halide.
19. The molecule of claim 1, wherein $X_1$ is haloalkylcarbonyl.
20. The molecule of claim 1, wherein $X_1$ is diazonium carbonyl.
21. The molecule of claim 1, wherein $R_1$ is —$(CH_2)_{11}$—.

* * * * *

UNITED STATES PATENT AND TRADEMARK OFFICE
CERTIFICATE OF CORRECTION

| | |
|---|---|
| PATENT NO. | : 7,770,437 B2 |
| APPLICATION NO. | : 11/637390 |
| DATED | : August 10, 2010 |
| INVENTOR(S) | : Frederix et al. |

It is certified that error appears in the above-identified patent and that said Letters Patent is hereby corrected as shown below:

| Issued Patent | | Description of Discrepancy |
|---|---|---|
| Column | Line | |
| Page 1 (Item 57) Abstract | 15 | Change "flurophenyl," to --fluorophenyl,--. |
| 2 | 8 | Change "bioreceptors" to --bioreceptors.--. |
| 2 | 56 | Change "thinly" to --thiol--. |
| 2 | 58 | Change "thinly" to --thiol--. |
| 3 | 20 | Change "create." to --create--. |
| 12 | 54 | Change "30," to --30.--. |
| 14 | 14 | Change "thinly" to --thiol--. |
| 22 | 38 (Approx.) | Change " $X_2=H,$ " to -- $X_2=H$,--. |
| 24 | 39 (Approx.) | Change " $X_2=H,$ " to -- $X_2=H$,--. |
| 26 | 33 | Change "thinly" to --thiol--. |
| 26 | 36 | Change " $X_2=H,$ " to -- $X_2=H$,--. |
| 28 | 58 (Approx.) | Change " $X_2=H,$ " to -- $X_2=H$,--. |
| 31 | 24 | Change " $X_2=H,$ " to -- $X_2=H$,--. |
| 36 | 66 | Change "mU" to --mL/--. |
| 38 | 14 | Change "thinly" to --thiol--. |
| 38 | 20 | Change "thinly" to --thiol--. |
| 38 | 23 (Approx.) | Change " $X_2=H.$ " to -- $X_2=H$.--. |

Signed and Sealed this
Twenty-second Day of February, 2011

David J. Kappos
*Director of the United States Patent and Trademark Office*

| Col. | Line | Correction |
|---|---|---|
| 40 | 53 (Approx.) | Change "(CH$_2$)$_n$" to --(CH$_2$)$_c$--. |
| 40 | 55 (Approx.) | Change "$X_2$=H" to --$X_2$=H--. |
| 41 | 62 | Change "evaporation" to --evaporation.--. |
| 44 | 14 (Approx.) | Change "$R_1$=(CH$_2$)$_{11}$ ." to --$R_1$=(CH$_2$)$_{11}$.--. |
| 47 | 26 | Change "$X_2$=H," to --$X_2$=H,--. |
| 49 | 8 (Approx.) | After "Synthesis of" delete "Synthesis of". (Second Occurrence) |
| 49 | 16 (Approx.) | Change "$X_2$=H," to --$X_2$=H,--. |
| 54 | 60 | Change "$X_2$=H," to --$X_2$=H,--. |
| 55 | 59 (Approx.) | Change "evaporation" to --evaporation.--. |
| 56 | 58 | Change "$X_2$=H," to --$X_2$=H,--. |
| 58 | 66 | Change "$X_2$=H," to --$X_2$=H,--. |
| 61 | 16 (Approx.) | After "Synthesis of" delete "Synthesis of ". (Second Occurrence) |
| 62 | 11 (Approx.) | Change "tetrafluorobenzylbromide" to --tetrafluorobenzylbromide.--. |
| 62 | 23 | Change "(CH$_2$)$_n$" to --(CH$_2$)$_c$--. |
| 62 | 24 | Before "pentafluorophenyl," insert --=--. |
| 62 | 24 | Change "$X_2$=H," to --$X_2$=H,--. |
| 62 | 24-25 | Change "$R_1$=(CH$_2$)$_{11}$ ," to --$R_1$=(CH$_2$)$_{11}$.--. |
| 65 | 44-45 (Approx.) | Change "Glycol" to --Glycols--. |
| 65 | 49-50 | Change "tetrafluorobenzoylchbride." to --tetrafluorobenzoylchloride.--. |
| 68 | 18 (Approx.) | In Claim 1, change "haloalklcarbonyl," to --haloalkylcarbonyl,--. |
| 68 | 18 (Approx.) | In Claim 1, change "carboxlic" to --carboxylic--. |
| 68 | 20 | In Claim 1, change "thiazolidinl" to --thiazolidinyl--. |
| 68 | 30 | In Claim 5, change "$X_1$" to --$X_1$.--. |